(12) United States Patent
Becker et al.

(10) Patent No.: US 6,225,061 B1
(45) Date of Patent: May 1, 2001

(54) SYSTEMS AND METHODS FOR PERFORMING REACTIONS IN AN UNSEALED ENVIRONMENT

(75) Inventors: Thomas Becker, Lineberg (DE); Hubert Köster, La Jolla, CA (US); Charles Cantor, Boston, MA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 09/266,409

(22) Filed: Mar. 10, 1999

(51) Int. Cl.$^7$ ........................................... C12Q 1/68
(52) U.S. Cl. .................... 435/6; 435/6; 435/177; 159/1; 159/47.1; 422/63; 422/64; 422/65; 422/66; 422/67; 436/177; 436/43
(58) Field of Search .................. 435/6, 177; 159/1, 159/47.1; 422/63, 64, 65, 66, 67; 436/177, 43

(56) References Cited

U.S. PATENT DOCUMENTS

| | | | |
|---|---|---|---|
| 4,418,576 | 12/1983 | White | 73/61.3 |
| 4,604,363 | * 8/1986 | Newhouse et al. | 436/177 |
| 4,725,677 | 2/1988 | Köster et al. | 536/27 |
| 4,920,264 | 4/1990 | Becker | 250/282 |
| 5,264,563 | 11/1993 | Huse | 536/25.3 |
| 5,270,163 | 12/1993 | Gold et al. | 435/6 |
| 5,503,980 | 4/1996 | Cantor | 435/6 |
| 5,547,835 | 8/1996 | Köster | 435/6 |
| 5,605,798 | 2/1997 | Köster | 435/6 |
| 5,622,824 | 4/1997 | Köster | 435/6 |
| 5,631,134 | 5/1997 | Cantor | 435/6 |
| 5,691,141 | 11/1997 | Köster | 435/6 |
| 5,777,324 | 7/1998 | Hillenkamp | 250/288 |
| 5,795,714 | 8/1998 | Cantor et al. | 435/6 |
| 5,851,765 | 12/1998 | Koster | 435/6 |
| 5,872,003 | 2/1999 | Koster | 435/283.1 |
| 5,900,036 | 5/1999 | Mossadegh et al. | 65/384 |
| 5,900,481 | 5/1999 | Lough | 536/55.3 |

FOREIGN PATENT DOCUMENTS

| | | |
|---|---|---|
| 0531234 | 3/1993 | (EP) . |
| 9416101 | 7/1994 | (WO) . |
| 9629431 | 9/1996 | (WO) . |
| 9708306 | 3/1997 | (WO) . |
| 9737041 | 10/1997 | (WO) . |
| 9742348 | 11/1997 | (WO) . |
| 9743617 | 11/1997 | (WO) . |
| 9820019 | 5/1998 | (WO) . |
| 9820020 | 5/1998 | (WO) . |
| 9820166 | 5/1998 | (WO) . |
| 9833052 | 7/1998 | (WO) . |
| 9833808 | 8/1998 | (WO) . |
| 9925724 | 5/1999 | (WO) . |

OTHER PUBLICATIONS

Belgrader et al., Rapid pathogen detection using a microchip PCR array instrument, *Clin Chem* 44(10):2191–4 (1998).
Blondelle et al., *Trends Anal. Chem.* 14:83–92 (1995).
Bowtell, Options available—from start to finish—for obtaining expression data by microarray, *Nature Genetics Supplement* 21:25–32 (1999).
Brown et al., *Molecular Diversity*, pp. 4–12 (1995).
Burns et al., Microfabricated structures for integrated DNA analysis, *Proc Natl Acad Sci USA* 93(11):5556–61 (1996).
C. Wentrup, "Reactive Molecules" (John Wiley & Sons) (1984).
Cantor et al., Instrumentation in molecular biomedical diagnostics: an overview, *Gentic Analysis* (Biomol. Eng.) 14:31–36 (1997).
Cheng et al., Chip PCR. II. Investigation of different PCR amplification systems in microbabricated silicon–glass chips, *Nucleic Acids Res* 24(2):380–5 (1996).
Cheung et al., Making and reading microarrays, *Nature Genetics Supp* 21:15–19 (1999).
Clark and Ewing, Experimenting in picoliter microvials, *Chemtech* Febr, pp. 20–25 (1998).
Eggers and Ehrlich, A review of microfabricated devices for gene–based diagnostics, *Hematologic pathology* 9(1):1–15 (1995).

(List continued on next page.)

*Primary Examiner*—W. Gary Jones
*Assistant Examiner*—Janell E. Taylor
(74) *Attorney, Agent, or Firm*—Stephanie L. Seidman; Heller Ehrman White & McAuliffe LLP

(57) ABSTRACT

An open system is provided for performing a submicroliter reaction. An open system can contain a solid support having a target site for performing the reaction; a liquid dispensing system such as a nanoliter dispensing pipette for dispensing a submicroliter amount of a liquid to the target site; a temperature controlling device for regulating the temperature of the support; and means for controlling the amount of liquid dispensed, which corresponds to the amount of liquid that evaporates from the target site. Also provided is an open system, including a solid support having a target site; a liquid dispensing system, which can dispense a liquid to the target site; a temperature controlling system, which regulates the temperature of the solid support; and an interface, which regulates an amount of liquid dispensed from the liquid dispensing system. Also provided is a method for performing a reaction in a submicroliter volume in an unsealed environment by dispensing a submicroliter volume of liquid onto the surface of a support; monitoring the temperature of the support; monitoring an amount or rate of evaporation of the liquid; and dispensing to the surface of the support a further amount of the liquid, which corresponds to the amount lost from the support due to evaporation, thereby maintaining the reaction volume at a predetermined volume throughout the course of the reaction. A method also is provided for maintaining a volume of a reaction mixture, which can be one of a plurality of reaction mixtures, on a solid support in an unsealed environment by monitoring the rate of evaporation of a liquid from the reaction mixture; and dispensing into the reaction mixture an amount of liquid that corresponds to the amount that evaporates.

71 Claims, 1 Drawing Sheet

OTHER PUBLICATIONS

Eggers et al., *Biotechniques* 17:516–525 (1994).
Eichler and Houghten, *Molec. Med. Today* 1:174–180 (1995).
Fattom et al., *Infect. Immun.* 60:584–589 (1992).
Fodor et al., Light–directed, spatially addressable parallel chemical synthesis, *Science* 251:767–773 (1991).
Fu et al., Sequencing exons 5 to 8 of the p53 gene by MALDI–TOF mass spectrometry, *Nat Biotechnol* 16(4):381–4 (1998).
Gallop et al., *J. Med. Chem.* 37:1233–1251 (1994).
Gildea, Köster et al., *Tetrahed. Lett.* 31:7095 (1990).
Gold et al., *Proc. Natl. Acad. Sci., USA* 94:59–64 (1997).
Goldmacher et al., *Bioconj. Chem.* 3:104–107 (1992).
Gordon et al., *J. Med. Chem.* 37:1385–1401 (1994).
Greene and Wuts, in "Protective Groups in Organic Synthesis" 2nd ed. (John Wiley & Sons) (1991).
Hadd et al., Microchip device for performing enzyme assays, *Anal Chem* 69(17):3407–12 (1997).
Hazum et al., in *Pept. Proc. Eur. Pept. Symp., 16th* (ed. K. Brunfeldt), pp. 105–110 (1981).
Instrumentation: Thermoelectric Modules from *Advanced Thermoelectric Products: Americool.* no date.
Instrumentation: Peltier Thermal Cycler, "PTC–200 DNA Engine" from *M.J. Research.*
Instrumentation: Thermoelectric Temperature Controllers from *Wavelenght Electronics.*
Instrumentation: TaqMan™ kit, from *Applied Biosystems,* distributed by Perkin Elmer.
Instrumentation: Nano Plotter from GeSiM.
Instrumentation: Thermocouples from *Newport Electronics.*
Instrumentation: Spectrochip from *Sequenom.*
IUPAC–IUB Commission on Biochemical Nomenclature [see, (1972) *Biochem.* 11: 1726].
Jacobson and Ramsey, Integrated microdevice for DNA restriction fragment analysis, *Anal. Chem.* 68:720–723 (1996).
Jurinke et al., Application of nested PCR and mass spectrometry for DNA–based virus detection: HBV–DNA detected in the majority of isolated anti–HBc positive sera, *Genetic Analysis* 14:97–102 (1998).
Kalinina et al., Nanoliter scale PCR with TaqMan detection, *Nucleic Acids Res* 25(10):1999–2004 (1997).
Köster et al., A strategy for rapid and efficient DNA sequencing by mass spectrometry, *Nature Biotech* 14:1123–1128 (1996).
Köster et al., N–ACYL proecting groups for deoxynucleosides, A quantitative and comparative study, *Tetrahedron* 37:363–369 (1981).
Köster et al., Oligonucleotide synthesis and multiplex DNA sequencing using chemiluminescent detection, *Nucl Acids Res* 24:318–321 (1991).
Köster et al., Polymer support oligonucleotide synthesis—XV[1,2], *Tetrahedron* 40:102–112 (1984).
Köster et al., et al., Some improvements in the synthesis of DNA of biological interest, *Nucl Acids Res* 7:39–59 (1980).
Köster et al., Well–defined insoluble primers for the enzymatic synthesis of oligo– and polynucleotides, *Hoppe–Seyler's Z. Physiol. Chem.* 359:11579–1589 (1978).
Li et al., High–Resolution MALDI Fourier Transform Mass Spectrometry of Oligonucleotides, *Anal Chem* 68:2090–2096 (1996).
Liang et al., *Science* 274:1520–1522 (1996).
Lins et al., Multiplex sets for the amplification of polymorphic short tandem repeat loci–silver stian and fluorescence detection, *Bio Techcniques* 20:882–889 (1996).
Little et al., *Anal. Chem.* 69:4540–4546 (1997).
Little et al., Direct detection of synthetic and biologically generated double–stranded DNA by MALDI–TOF MS, *Int. J. Mass Spec Ion Processes 170:* 133–140 (1997).
Little et al., Mass spectrometry from miniaturized arrays for full comparative DNA analysis, *Nature Med 3:*1413–1416 (1997).
Little et al., *Int. J. Mass Spectrom. Ion Processes* 169/170:323–330 (1997).
Mathies et al., Capillary array electrophoresis: an approach to high–speed, high–throughput DNA sequencing, *Nature* 359:167–169 (1992).
McGall et al., Light–directed synthesis of high–density oligonucleotide arrays using semiconductor photoresists, *Proc. Natl. Acad. Sci. USA* 93:13555–13560 (1996).
Melcor Thermoelectric Product Information, available at Jan. 27, 1999.
Melcor Thermolectic FAQ, available at http:/, Jan. 27, 1999.
Nanoplotter no date.
Nielsen et al., *Science* 254:1497 (1991).
Nyren, *Anal. Biochem.* 167:235–238 (1987).
O'Donnell et al., High–density, covalent attachment of DNA to silicon wafers for analysis by MALDI–TOF mass spectrometry, *Anal. Chem.* 69:2438–2443 (1997).
Olejnik, Rothschild et al., *Nucl. Acids Res.* 24:361–66 (1996).
Peltier Thermal Cycler, The PTC–200 Engine, available at http://, Mar. 4, 1999.
Quniton, *Appl. Physiol.* 1976 Feb., 40(2): 260–2.
R. Foster, "Organic Charge Transfer Complexes" (Academic Press) (1969).
Reznik et al., A streptavidin mutant with altered ligand–binding specificity, *Proc. Natl. Acad. Sci. USA* 95:13525 (1998).
Ronaghi et al., *Anal. Biochem.* 267:65–71 (1999).
Ronaghi et al., *Anal.Biochem.* 242:84–89 (1996).
Ronaghi et al., *Biotechniques* 25:876–878, 880–882, and 884 (1998).
Ronaghi et al., *Science* 281:363–365 (1998).
Ross et al., Analysis of DNA fragments from conventional and microfabricated PCR devices using delayed extraction MALDI–TOF mass spectrometry, *Anal. Chem.* 70(10):2067–73 (1998).
S.M. Hecht, ed. "Bioorganic Chemistry: Nucleic acids" (Oxford Univ. Press 1996) Hecht, ed. "Bioorganic Chemistry: Nucleic acids" Oxford Univ. Press 1996, pp. 36–74).
Sambrook et al., Maxam–Gilbert Chemical Degradation of DNA method, "Molecular Cloning: A laboratory manual" 2nd ed. (Cold Spring Harbor Laboratory Press 1989), pp. 13.11–13.13.
Senter et al., *Photochem. Photobiol* 42:231–237 (1985).
Sequenom Advances the Industrial Genomics Revolution with the Launch of Its DNA MassArray™Automated Process Line, Press Release: Sep. 28, 1998, http://.
Sequenom Obtains Important New Patent for MassArray Technology, Press Release: May 24, 1999.
Sequenom Obtains Patent for Combing DNA Amplification and Sequencing as Part of its MassArray Technology, Press Release: Aug 25, 1999.
Sequenom Obtains Patents for MassArray Technology, Press Release: April 27, 1999.

Sequenom Uses DNA MassArray™ to Sequence Section of Human Cancer–Related p53 Gene, Press Release: Mar. 27, 1998.

Simpson et al., High–throughput gentic analysis using microfabricated 96–sample capillary array electrophoresis microplates, *Proc. Natl. Acad. Sci. USA* 95:2256–2261 (1998).

Tang et al., Matrix–assisted laser desorption/ionization mass spectrometry of immobilized duplex DNA probes, *Nucleic Acids Research* 23:3126–3131 (1995).

Thermoelectric Modules (Americool) no date.

van den Boom et al., Combined amplification and sequencing in a single reaction using two DNA polymerases with differential incorporation rates for dideoxynucleotides, *J. Biochem. Biophys Methods* 35(2):69–79 (1997).

van den Boom et al., Anal. Biochem. 256: 127–129.

Wang et al., Large–scale identification, mapping, and genotyping of single–nucleotide polymorphisms in the human genome, *Science* 280:1077–1082 (1998).

Waters et al., Microchip device for cell lysis, multiplex PCR amplification, and electrophoretic sizing, *Anal. Chem.* 70:158–162 (1998).

Waters et al., Multiple sample PCR amplification and electrophoretic analysis on a microchip, *Anal Chem* 70(24):5172–6 (1998).

Weiler et al., Hybridisation based DNA screening on peptide nucleic acid (PNA) oligomer arrays, *Nucleic Acids Res.* 25:2792–2799 (1997).

Welhöner et al., *J. Biol. Chem.* 266:4309–4314 (1991).

Whittal et al., Nanoliter chemistry combined with mass spectrometry for peptide mapping of proteins from single mammalian cell lysates, *Anal Chem* 70(24):5344–7 (1998).

Woolley et al., Functional integration for PCR amplification and capillary electrophoresis in a microfabricated DNA analysis device, *Anal. Chem.* 68:4081–4086 (1996).

Yen et al., *Makromol. Chem* 190:69–82 (1989).

Derwent ™009385238, WPI Acc. No. 1993–078716/199310, citing European Patent No. EP 0 531 234 published Mar. 10, 1993 (item B).

Lemmo et al., "Characterization of an inkjet chemical microdispenser for combinatorial library synthesis", *Anal. Chem.* 69:543–551 (1997).

Litborn et al., "Parallel reactions in open chip–based nanovials with continuous compensation for solvent evaporation", *Electrophoresis* 21:91–99 (2000).

\* cited by examiner-

SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthesized
      primer
<220> FEATURE:
<221> NAME/KEY: primer_bind
<222> LOCATION: (1)..(25)
<223> OTHER INFORMATION: Forward PCR primer for human B-actin gene

<400> SEQUENCE: 1
tcacccacac tgtgcccatc tacga                                           25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:  Synthetic
      primer
<220> FEATURE:
<221> NAME/KEY: primer_bind
<222> LOCATION: (1)..(25)
<223> OTHER INFORMATION: Reverse PCR primer for human B-actin gene

<400> SEQUENCE: 2
cagcggaacc gctcattgcc aatgg                                           25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(25)
<223> OTHER INFORMATION: dual fluorophore-labeled probe that is
      complementary to B-actin specific PCR product
<220> FEATURE:
<221> NAME/KEY: modified_base
<222> LOCATION: (1)
<223> OTHER INFORMATION: 6-carboxyfluorescein at 5'-end
<220> FEATURE:
<221> NAME/KEY: modified_base
<222> LOCATION: (7)
<223> OTHER INFORMATION: 6-carboxytetramethyl-rhodamine - labeled
      cytosine at position 7

<400> SEQUENCE: 3 atgcccccccc catgccatcc tgcgt                                          25

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:  Synthetic
      primer
<220> FEATURE:
<221> NAME/KEY: primer_bind
<222> LOCATION: (1)..(23)
<223> OTHER INFORMATION: Forward PCR primer for 389 bp human B-actin
      cDNA insert
<220> FEATURE:

```
<221> NAME/KEY: modified_base
<222> LOCATION: (1)
<223> OTHER INFORMATION: Biotinylation at the 5'-end

<400> SEQUENCE: 4
gactgactac ctcatgaaga tcc                                              23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: primer_bind
<222> LOCATION: (1)..(20)
<223> OTHER INFORMATION: Reverse PCR primer for 389 bp human B-actin
      cDNA insert

<400> SEQUENCE: 5
gaagctgtag ccgcgctcgg                                                  20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: primer_bind
<222> LOCATION: (1)..(18)
<223> OTHER INFORMATION: Forward amplification primer directed against
      exon 7 of human p53 gene

<400> SEQUENCE: 6
ctgcttgcca caggtctc                                                    18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: primer_bind
<222> LOCATION: (1)..(18)
<223> OTHER INFORMATION: Reverse amplification primer directed against
      exon 7 of the human p53 gene
<220> FEATURE:
<221> NAME/KEY: modified_base
<222> LOCATION: (1)
<223> OTHER INFORMATION: 5'-biotinylated primer

<400> SEQUENCE: 7
cacagcaggc cagtgtgc                                                    18

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: primer_bind
<222> LOCATION: (1)..(16)
<223> OTHER INFORMATION: Sequencing primer for exon 7 of human p53 gene
```

-continued

<400> SEQUENCE: 8
gaggcccatc ctcacc                                                                    16

SYSTEMS AND METHODS FOR PERFORMING REACTIONS IN AN UNSEALED ENVIRONMENT

BACKGROUND OF THE INVENTION

1. Field of the Invention

The invention relates generally to systems and methods for performing a reaction in a small volume without incurring an undesirable loss of the reaction volume due to evaporation, and more specifically to systems and methods for performing reactions involving polymers, particularly biopolymers, in a reaction volume of a few microliters or less in an unsealed environment.

2. Background Information

Technological advances have allowed an examination of previously undiscernible phenomena. Such advances are particularly notable in the biological sciences, where the chemical and physical structures of many biopolymers have been described, and where such biopolymers, including DNA and proteins, routinely are synthesized and sequenced.

Although methods such as nucleic acid sequencing and synthesis have contributed to understanding the structure and function of biological molecules and their relationships to disease, the limitations of such methods are apparent. For example, it generally is agreed that knowledge of the entire sequence of the human genome would provide valuable insight into the prevention and treatment of disease. The human genome, however, contains over one billion nucleotides and a huge expenditure of labor and money would be required to sequence the entire human genome. Furthermore, using currently available methods, many years will be required to see the project to completion.

Similarly, it is a goal of most clinical researchers to develop rapid and simple tests for determining whether an individual has a disease or predisposition to a disease. In many cases, the signs and symptoms of many genetic diseases do not become apparent until an individual reaches a certain age or stage of development. Knowledge that an individual has a predisposition to a genetic disease can allow the clinician to take prophylactic measures to minimize or delay onset of the disease. Ideally, all individuals would be screened for potential genetically determined diseases, including screening a large number of genes in each individual. Unfortunately, such routine screening currently is not feasible because the assays are time consuming and the reagents for performing such assays are expensive and limited in availability.

In an effort to reduce the time and cost for analyzing biopolymers, including genes and proteins, processes are being developed to automate the analytic procedures. Automation provides a means for performing repetitive processes almost continually, except for periodic breaks for equipment maintenance, and allows researchers and technical staff to devote more time to other endeavors, including interpreting the results produced by the automated assays and troubleshooting problems that may arise. Automation of repetitive processes also provides the advantage that the likelihood of errors occurring, for example, due to fatigue or distraction is reduced and, therefore, more accurate results can be obtained.

The application of nanotechnology to the biological sciences promises to provide the next breakthroughs relating, for example, to the analysis, synthesis and utilization of biopolymers. Nanotechnology, which provides processes and apparatuses for performing procedures on a very small scale, has been developed by the semiconductor industry in order to produce smaller and smaller microchips, and to allow placement of a continually increasing number of instructions on a microchip.

Efforts are in progress to apply nanotechnology to chemical and biological procedures, thereby providing a means to perform assays in very small volumes, generally a few hundred nanoliters or less. Application of nanotechnology to biological assays can be particularly valuable because a critical limitation of many biological assays is the amount of biological material available for analysis. By performing such assays in nanoliter volumes or smaller, the effective concentration of a biopolymer in a biological reaction is increased, thereby providing the necessary kinetics for a biological reaction to proceed. In addition, the ability to perform biological assays in nanoliter volumes can provide a significant cost savings because much smaller amounts of reagents, which can be very expensive, can be utilized in the reactions.

The application of nanotechnology to biological assays has been hindered, in part, by the difficulty in manipulating and maintaining such small volumes. Many biological assays, for example, are performed in aqueous conditions, using water as a solvent, and at elevated temperatures, generally at least 37° C., which is human body temperature. Water, like many liquid solvents, is susceptible to evaporation and, therefore, as the time or temperature of a reaction increases, the loss of water due to evaporation increases and the volume of the reaction decreases. As a result of evaporation, the effective concentration of reagents in the reaction increases, thereby changing the conditions of the reaction. Since most biological assays are quite sensitive to reaction conditions, loss of water or other solvent from a reaction can result in an assay that produces spurious results. Any loss of a solvent such as water is particularly deleterious when the reaction contains only a few hundred nanoliters or less of the liquid, since the reaction quickly can evaporate to dryness.

Various methods have been used to minimize the loss of solvent in a reaction due to evaporation in biochemical assays. For example, reaction mixtures can be drawn into glass capillary tubes, which then are sealed at both ends for the reaction. Small volume glass capillary tubes can be expensive, and the use of such tubes requires additional steps, including sealing and unsealing the tube, the latter which can produce glass shards.

In many cases, reaction mixtures are performed in a microcentrifuge tube or other open chamber, and evaporation is minimized by overlaying the reaction mixture with wax, mineral oil, or other nonvolatile compound during the reaction. Such a method, again, requires additional steps, including removing the sealing material following the reaction. In order to remove all or most of the sealing material, which can otherwise contaminate the sample and hinder further analysis, some loss of the sample being assayed inevitably occurs. Since most biological samples are limited to begin with, any loss of sample can preclude an interpretation of the results of the assay. In general, any additional manipulations of a sample will incur extra cost, either in terms of time or money, and loss or contamination of the sample.

More recently, biological reactions have been performed on microchips, which conveniently can be adapted to automated processes. Such microchips have been designed having a system including, for example, chambers, which hold the reactants, and channels, which connect the chambers and in which the reactants can be mixed and a reaction performed. Since the channels, in which the reaction occurs, provide a sealed or closed environment, there is little or no evaporative loss of the reaction volume. Thus far, however, the technology for preparing such a device allows for the placement of only one or few of such closed systems on a single microchip and, therefore, the number of reactions that can be performed at one time on a single chip is limited. Thus, a need exists for systems useful for performing reactions in a volume of a few microliters or less in an unsealed environment. Therefore it is an object here to provide systems and methods that satisfy this need and also provide additional advantages.

SUMMARY OF THE INVENTION

Systems are provided for performing a reaction in an unsealed environment. The systems are used for any desired reaction, including, but not limited to in situ biopolymer or polymer synthesis, such as nucleic acid and protein syntheses, protein and nucleic acid sequencing methods, such as oligonucleotide-based primer extension, nucleic acid amplification reactions, protein and nucleic acid protease- or nuclease-based degradations and others.

A system as disclosed herein is an open system for performing a reaction, such as a synthetic reaction or an assay, particularly in a submicroliter volume. The systems can include a support for performing the reaction; a nanoliter dispensing pipette for dispensing a submicroliter amount of a liquid to a target site on the support; a temperature controlling device for regulating the temperature of the surface of the support; and means for controlling the amount of liquid dispensed, where the amount of liquid dispensed corresponds to the amount of liquid evaporated from the support. A means for controlling the amount of liquid dispensed can include computer software that calculates the rate of evaporation and signals the dispensing pipette to deliver an amount of the liquid that corresponds to the amount lost due to evaporation. A means for controlling the amount of liquid dispensed also can be manual input, which can be performed by an individual.

A system as disclosed herein also can include a temperature measuring device for measuring the temperature of the surface of the support. The support can be any support having a surface, including, for example, a bead, pin, comb, wafer, well or microchip, and the support can be functionalized such that a substrate, for example, a biopolymer can be linked, either directly or indirectly via covalent or non-covalent interactions, to the support and immobilized.

An open system, as disclosed herein, also can include a solid support, which has a target site that can contain a volume of liquid, for example, a reaction mixture; a liquid dispensing system, which can dispense a liquid to the target site; a temperature controlling system, which can regulate the temperature of the solid support; and an interface, which can indicate an amount of liquid to be dispensed to the target site from the liquid dispensing system. An interface can include, for example, a computer using an appropriate algorithm. A computer can monitor the temperature of the solid support and, based on various parameters, including, for example, the chemical nature of the liquid, the surface area of the liquid exposed to the environment, and the time the liquid is maintained at a particular temperature, and can provide information as to the amount of liquid to be dispensed from the liquid dispensing system to the target site to maintain the liquid at a predetermined volume. Based on that information, the liquid dispensing system can be manipulated manually, to dispense the liquid to the target site, or can be controlled automatically, for example, by interfacing it with the computer. In a system as disclosed herein, the amount of liquid dispensed from a liquid dispensing system to a target site generally corresponds to an amount of liquid lost from the target site due to evaporation, although the amount added also can be an initial amount added to a target site or an amount added to modify the conditions of a reaction.

An open system, as disclosed herein, also can include a solid support having a target site; a liquid dispensing system, which can dispense a liquid to the target site; a temperature controlling system, which regulates the temperature of the solid support; and means for regulating an amount of liquid dispensed from the liquid dispensing system. In addition, an open system, as disclosed herein, can have a means for containing a reaction mixture; a means for dispensing a liquid; a means for controlling the temperature of the reaction volume containing means; and means for regulating an amount of liquid dispensed from the liquid dispensing means.

A means for regulating an amount of liquid dispensed can be a computer having an appropriate algorithm. Such a computer can interface with the solid support, thereby monitoring the temperature of the support, and can provide an indication of an amount of liquid to be dispensed to a target site to maintain a predetermined volume, for example, of a reaction volume. The computer can cause to be displayed the amount of liquid to be dispensed, such that an individual can manipulate the liquid dispensing system and dispense the liquid, or the computer can further interface with the liquid dispensing system, thereby causing the amount of liquid to be dispensed. In addition, charts can be developed that predict the amount and rate of evaporation of a particular solvent at a particular temperature and, based on such charts, an individual can manipulate the liquid dispensing system as necessary. Also, a decrease in the volume of a liquid due to evaporation can be identified directly by including the liquid in a circuit, wherein, when the liquid falls below a predetermined point, the circuit is broken, thereby indicating that a liquid should be dispensed to the target site until the circuit is reestablished.

Methods for maintaining a volume of a liquid in an unsealed environment also are provided. A method for performing a reaction in a predetermined submicroliter volume in the open can be performed by dispensing the predetermined submicroliter volume of liquid onto the surface of a support; optionally monitoring the temperature of the substrate; determining the amount or rate of evaporation of the liquid from the support; and dispensing a further amount of the liquid to the surface of the support, wherein the further amount dispensed corresponds to the amount lost from the support due to evaporation, thereby maintaining the reaction volume at a predetermined volume throughout the course of the reaction. Such a method also can be performed, for example, by determining the temperature of a solid support, which has a target site that can contain a volume of liquid; and, based on the temperature, dispensing at the target site an amount of liquid required to maintain a predetermined volume of the liquid. The amount of liquid to be dispensed can be determined using a computer algorithm, which, based on various parameters, including the temperature of the support, the chemical nature of the liquid, the surface area of the liquid exposed to the environment, and the volume to be maintained, can indicate the amount of liquid that evaporates from the site and, therefore, the amount of liquid to be dispensed to maintain a predetermined volume. The volume of a liquid on a target site also can be monitored, for example, by microscopic examination, using an appropriate optical system or a video imaging device, such that, as the volume of a liquid at a target site decreases due to evaporation, a corresponding amount of liquid can be dispensed to maintain the volume within acceptable parameters.

Methods for performing a reaction in an unsealed environment also are provided. Such a method can be performed, for example, by determining the temperature of a solid support, which has a target site containing a volume of the reaction mixture, or determining the rate or amount of evaporation of liquid from the reaction mixture; and dispensing into the reaction mixture an amount of liquid required to maintain the volume at a predetermined level. Such a method is particularly useful where the reaction mixture has a volume of a few microliters or less, particularly a volume of about 500 nanoliters or less. The disclosed methods also are useful for performing submicroliter reactions at temperatures where the vapor pressure of a liquid in the reaction mixture is undesirably high, for example, about 2.5 kiloPascals (kPa) or greater, particularly about 5 kPa or greater, or about 10 kPa or greater, such that evaporation of the liquid can substantially change the volume of the reaction mixture and adversely affect the reaction. As such, the disclosed methods are useful for performing various chemical, physical and biological reactions, for example, a polymerase chain reaction, or a nucleic acid or polypeptide synthesis or sequencing reaction or other reaction or assay performed on a solid support.

DETAILED DESCRIPTION OF THE INVENTION

Figure 1:
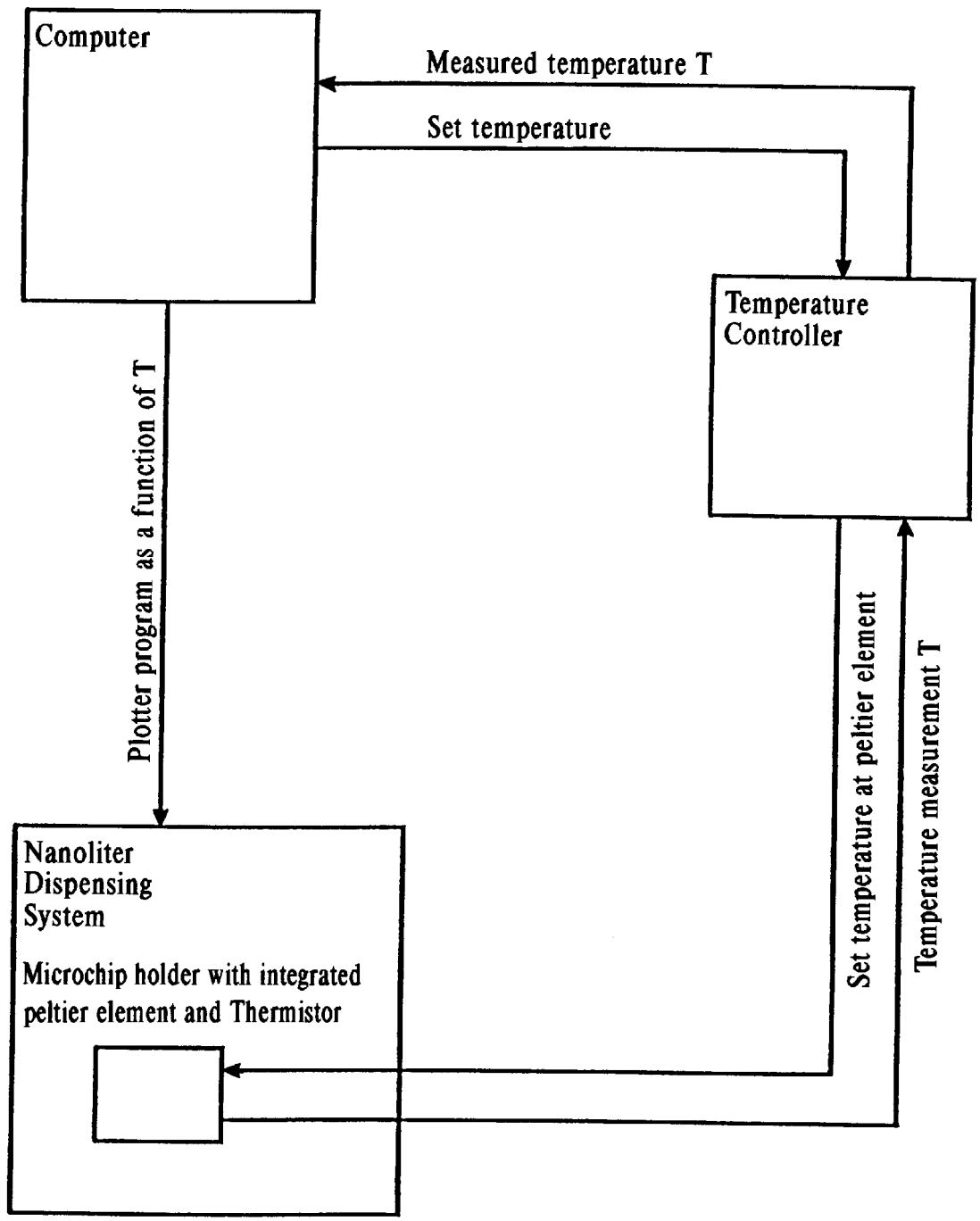
FIG. 1 provides an exemplary embodiment of an open system for performing a reaction in an unsealed environment. A liquid is contained on a target site on the surface of a microchip, which is in a holder that is integrated with a Peltier element and thermistor. The temperature of the Peltier element/thermistor is regulated by a temperature controller, which is interfaced with a computer, and the temperature of the chip is monitored. The computer, which also is interfaced with the nanoliter dispensing device, receives input of the measured temperature, calculates the amount of liquid that evaporates from the target site, and signals the dispensing device to dispense an amount of liquid that corresponds to the amount that evaporates, thereby maintaining the volume of liquid on the target site at a predetermined level.

A system is provided for performing reactions in an unsealed environment, including reactions performed in submicroliter volumes. An open system as disclosed herein solves the previously intractable problems caused by evaporation of a liquid solvent during a reaction, including, for example, the concomitant increase in the effective salt concentration, which can inhibit a reaction or lead to spurious results. An additional advantage of the disclosed open systems and methods of performing a reaction in an unsealed environment is that fewer steps are required to perform a reaction because the reaction volume need not be sealed or covered with a protective layer such as mineral oil to prevent evaporation, such manipulations further requiring that the volume later be unsealed or isolated from the protective layer. As a result, the likelihood that any sample will be lost due to the additional manipulations is reduced.

An open system as disclosed herein provides the further advantage that "single tube" reactions can be performed, wherein a number of different reactions are performed at the same target site. The ability to perform single tube reactions further reduces the likelihood that any sample will be lost due to transferring a material from one tube to another for performing different reactions, and facilitates the automation of chemical and biological reactions. It should be recognized that such reactions, while referred to as "single tube" reactions, need not literally be performed in a "tube," but can be performed at any target site having the characteristics disclosed herein.

The disclosed open systems are useful for performing liquid handling, for example, for performing reactions such as polymerase chain reaction (PCR), DNA sequencing and enzymatic digestion reactions. Such reactions can be performed directly on the surface of a modified silicon chip that can be used for mass spectrometric detection of the resulting products, or allows on-line monitoring of fluorescent or luminescent signals. It is important to prevent evaporation of a solvent, generally water, of a reaction to prevent alterations in concentrations of reactants or other components such as salts during the reactions. Typically, evaporation is prevented by performing reactions in sealed or closed environments. The methods and systems disclosed herein permit reactions to be performed, for example, directly on the surface of a microchip without a need for a lid or sealing. This achieved by replacing nanoliter amounts of water or water/glycerol or other reaction mixture components in the reaction mixture using drop-on-demand systems, which compensate for loss of solvent by evaporation.

An open system as disclosed herein can include a support for performing the reaction; a nanoliter dispensing pipette for dispensing a submicroliter amount of a liquid onto the surface of the support; a temperature controlling device for regulating the temperature of a target site on the support, particularly of a liquid at the target site; and means for controlling the amount of liquid dispensed, wherein the amount of liquid dispensed corresponds to the amount of evaporation of a the liquid from the support. A system as disclosed herein also can include a temperature measuring device for measuring the temperature of the surface of the support. The support can be any support having a surface, including, for example, a bead, pin, comb, wafer, well or microchip, and the support can be functionalized such that a biopolymer can be linked to the support and immobilized.

A means for controlling the amount of liquid dispensed can include computer software that calculates the rate or amount of evaporation of the liquid and signals the dispensing pipette to deliver an amount of the liquid that corresponds to the amount lost due to evaporation. A means for controlling the amount of liquid dispensed also can be manual input, which can be performed by an individual. In addition, a means for controlling the amount of liquid dispensed can be a system that determines when a meniscus of a liquid decreases below a predetermined point. Such a system can be, for example, an electrical circuit, which is broken when the meniscus falls below a predetermined point; or a photometric or spectrophotometric system, which detects a change in diffraction, transmission or absorbance of photons when the meniscus falls below a predetermined point. Such a meniscus determining means conveniently can provide an interface between the target site and the liquid dispensing system. A means for controlling the amount of liquid dispensed also can be a system for determining the conductivity (or resistivity) of the liquid, which changes in parallel with a change in the reaction volume, such that, when the conductivity (or resistivity) reaches a predetermined value, an indication is provided as to an amount of liquid to be dispensed to the target site to the maintain the liquid at a predetermined volume.

An open system as disclosed allows a reaction to be performed in an unsealed environment. An open system can include a solid support, which has a target site that contains the reaction mixture; a liquid dispensing system; a temperature controlling system, which regulates the temperature of the solid support; and an interface that regulates an amount of liquid dispensed from the liquid dispensing system. The interface can indicate an amount of liquid to be dispensed based, for example, on the temperature of the solid support or the decrease of a meniscus below a predetermined point, and the amount of liquid dispensed can correlate with the amount of liquid that evaporates from a reaction mixture on the solid support. Also provided is a system having means for dispensing a liquid; means for containing a reaction volume; means for controlling the temperature of the reaction volume containing means; and means for regulating an amount of liquid dispensed from the liquid dispensing means based on the temperature of the reaction volume containing means. A means for containing a reaction volume can be a solid support having, for example, a well or pin, or a barrier, which can be a physical or chemical barrier.

Definitions

Unless defined otherwise, all technical and scientific terms used herein have the same meaning as is commonly understood by one of skill in the art to which this invention belongs. All patents, pending and published applications and publications referred to herein are incorporated by reference.

As used herein, the term "unsealed environment," when used in reference to a volume of a liquid, means that there is no particular barrier present to prevent substantial evaporation of the liquid into the environment. For purposes herein, substantial evaporation occurs when evaporation occurs at a rate or amount that alters the reaction conditions before the reaction of interest is completed. This is particularly problematic for reactions that are performed in wells or on the surface of solids small volumes, typically submicroliter volumes. Hence, methods and systems are provided herein to permit such reactions to be performed.

As used herein, an open system refers to the systems disclosed herein for maintaining a volume of a liquid in an unsealed environment. These can be referred to generally as "open systems" although such systems can be sealed from the air, such as under inert gas or in a box or other container. As noted an open system is one in which evaporation occurs during the reaction of interest in an amount or rate such that conditions of the reaction are altered, such by a change in concentration of critical components, such as salt concentrations. This will occur if small volume, such as submicroliter reactions, are performed in wells or on the surface of a solid support. The disclosed systems and methods, thus, are distinguishable from systems and methods for performing a reaction, for example, in an unsealed microcapillary tube or in a channel on a microchip because, even though a liquid may be in direct contact to the open air in such systems, the amount of evaporation that occurs is not unacceptable either because the evaporation is desired, or because the surface area of the liquid in contact with the gaseous medium is so small with respect to the volume of the liquid that any evaporation that occurs during the reaction period does not deleteriously affect or alter the reaction conditions.

As used herein, the term "liquid dispensing system" means a device that can transfer a predetermined amount of liquid to a target site. The amount of liquid dispensed and the rate at which the liquid dispensing system dispenses the liquid to a target site, which can contain a reaction mixture, can be adjusted manually or automatically, thereby allowing a predetermined volume of the liquid to be maintained at the target site.

As used herein, the term "liquid" is used broadly to mean a non-solid, non-gaseous material, which can be homogeneous or heterogeneous and can contain one or more solid or gaseous materials dissolved or suspended therein. In general, a liquid is a component of a reaction mixture that is susceptible to evaporation under the conditions of the reaction. In particular, the liquid can be a solvent, in which a reaction is performed, for example water or glycerol/water or buffer or reaction mixture, where the reaction is performed in an aqueous solution. The liquid can be any non-solid, non-gaseous solvent or other component of a reaction mixture that is susceptible to evaporative loss, for example, acetonitrile, which can be a solvent for a nucleic acid synthesis reaction; formamide, which can be a liquid component of a nucleic acid hybridization reaction; piperidine, which is a liquid component of a nucleic acid sequencing reaction; or any other non-aqueous solvent or other liquid component. A liquid can contain dissolved or suspended components, which can be useful, for example, for initiating, terminating or changing the conditions of a reaction, thereby facilitating the performance of single tube reactions.

As used herein, the term "reaction mixture" refers to any solution in which a chemical, physical or biological change is effected. In general, a change to a molecule is effected, although changes to cells also are contemplated. A reaction mixture can contain a solvent, which provides, in part, appropriate conditions for the change to be effected, and a substrate, upon which the change is effected. A reaction mixture also can contain various reagents, including buffers, salts, and metal cofactors, and can contain reagents specific to a reaction, for example, enzymes, nucleoside triphosphates, amino acids, and the like. For convenience, reference is made herein generally to a "component" of a reaction, wherein the component can be a cell or molecule present in a reaction mixture, including, for example, a biopolymer or a product thereof.

As used herein, the term "biopolymer" is used to mean a biological molecule composed of two or more monomeric subunits, or derivatives thereof, which are linked by a bond or a macromolecule. A biopolymer can be, for example, a polynucleotide, a polypeptide, a carbohydrate, or a lipid, or derivatives or combinations thereof, for example, a nucleic acid molecule containing a peptide nucleic acid portion or a glycoprotein, respectively. The methods and systems herein, though described with reference to biopolymers, can be adapted for use with other synthetic schemes and assays, such as organic syntheses of pharmaceuticals, or inorganics and any other reaction or assay performed on a solid support or in a well in nanoliter volumes.

As used herein, a biological particle refers to a virus, such as a viral vector or viral capsid without or without packaged nucleic acid, phage, including a phage vector or phage capsid, with or without encapsulated nucleotide acid, a single cell, including eukaryotic and prokaryotic cells or fragments thereof, and other such biological materials.

As used herein, the term "polynucleotide" refers to an oligomer or polymer containing at least two linked nucleotides or nucleotide derivatives, including a deoxyribonucleic acid (DNA), a ribonucleic acid (RNA), and a DNA or RNA derivative containing, for example, a nucleotide analog or a "backbone" bond other than a phosphodiester bond, for example, a phosphotriester bond, a phosphoramidate bond, a phophorothioate bond, a thioester bond, or a peptide bond (peptide nucleic acid). The term "oligonucleotide" also is used herein essentially synonymously with "polynucleotide," although those in the art will recognize that oligonucleotides, for example, PCR primers, generally are less than about fifty to one hundred nucleotides in length.

Nucleotide analogs contained in a polynucleotide can be, for example, mass modified nucleotides, which allows for mass differentiation of polynucleotides; nucleotides containing a detectable label such as a fluorescent, radioactive, luminescent or chemiluminescent label, which allows for detection of a polynucleotide; or nucleotides containing a reactive group such as biotin or a thiol group, which facilitates immobilization of a polynucleotide to a solid support. A polynucleotide also can contain one or more backbone bonds that are selectively cleavable, for example, chemically, enzymatically or photolytically. For example, a polynucleotide can include one or more deoxyribonucleotides, followed by one or more ribonucleotides, which can be followed by one or more deoxyribonucleotides, such a sequence being cleavable at the ribonucleotide sequence by base hydrolysis. A polynucleotide also can contain one or more bonds that are relatively resistant to cleavage, for example, a chimeric oligonucleotide primer, which can include nucleotides linked by peptide nucleic acid bonds and at least one nucleotide at the 3' end, which is linked by a phosphodiester bond, or the like, and is capable of being extended by a polymerase. Peptide nucleic acid sequences can be prepared using well known methods (see, for example, Weiler et al., *Nucleic acids Res.* 25:2792–2799 (1997)).

A polynucleotide can be a portion of a larger nucleic acid molecule, for example, a portion of a gene, which can contain a polymorphic region, or a portion of an extragenic region of a chromosome, for example, a portion of a region of nucleotide repeats such as a short tandem repeat (STR) locus, a variable number of tandem repeats (VNTR) locus, a microsatellite locus or a minisatellite locus. A polynucleotide also can be single stranded or double stranded, including, for example, a DNA-RNA hybrid, or can be triple stranded or four stranded. Where the polynucleotide is double stranded DNA, it can be in an A, B, L or Z configuration, and a single polynucleotide can contain combinations of such configurations.

As used herein, the term "polypeptide," means at least two amino acids, or amino acid derivatives, including mass modified amino acids and amino acid analogs, that are linked by a peptide bond, which can be a modified peptide bond. A polypeptide can be translated from a polynucleotide, which can include at least a portion of a coding sequence, or a portion of a nucleotide sequence that is not naturally translated due, for example, to it being located in a reading frame other than a coding frame, or it being an intron sequence, a 3' or 5' untranslated sequence, a regulatory sequence such as a promoter, or the like. A polypeptide also can be chemically synthesized and can be modified by chemical or enzymatic methods following translation or chemical synthesis. The terms "polypeptide," "peptide" and "protein" are used essentially synonymously herein, although the skilled artisan will recognize that peptides generally contain fewer than about fifty to one hundred amino acid residues, and that proteins often are obtained from a natural source and can contain, for example, post-translational modifications. A polypeptide can be post-translationally modified by phosphorylation (phosphoproteins), glycosylation (glycoproteins, proteoglycans), and the like, which can be performed in a cell or in a reaction in vitro.

As used herein, a reaction mixture used in an open system or method as disclosed herein can have any volume from a few picoliters or less to hundreds of liters or more. An open system or method as disclosed herein is particularly useful where a volume to be maintained is critical in order for a reaction to occur, and where the volume to be maintained is not amenable to simple inspection or measurement. As such, the disclosed systems and methods generally are useful where the reaction volume is about 500 milliliters or less; are more useful where the reaction volume is about 5 milliliters or less; are most useful where the reaction volume is in the "submilliliter" range, for example, about 500 microliters, or about 50 microliters or about 5 microliters or less; and are particularly useful where the reaction volume is a "submicroliter" reaction volume, which can be measured in nanoliters, for example, about 500 nanoliters or less, or 50 nanoliters or less or 10 nanoliters or less, or can be measured in picoliters, for example, about 500 picoliters or less or about 50 picoliters or less. For convenience of discussion, the term "submicroliter" is used herein to refer to a reaction volume less than bout one microliter, although it will be readily apparent to those in the art that the systems and methods disclosed herein are applicable to subnanoliter reaction volumes as well. A reaction mixture is contained in or on a target site on a solid support.

As used herein, the term "solid support" means a non-gaseous, non-liquid material having a surface. Thus, a solid support can be a flat surface constructed, for example, of glass, silicon, metal, plastic or a composite; or can be in the form of a bead such as a silica gel, a controlled pore glass, a magnetic or cellulose bead; or can be a pin, including an array of pins suitable for combinatorial synthesis or analysis.

As used herein, the term "target site" refers to a specific locus on a solid support that can contain a liquid. A solid support contains one or more target sites, which can be arranged randomly or in ordered array or other pattern. In particular, a target site restricts growth of a liquid to the "z" direction of an xyz coordinate. Thus, a target site can be, for example, a well or pit, a pin or bead, or a physical barrier that is positioned on a surface of the solid support, or combinations thereof such as a beads on a chip, chips in wells, or the like. A target site can be physically placed onto the support, can be etched on a surface of the support, can be a "tower" that remains following etching around a locus, or can be defined by physico-chemical parameters such as relative hydrophilicity, hydrophobicity, or any other surface chemistry that allows a liquid to grow primarily in the z direction. A solid support can have a single target site, or can contain a number of target sites, which can be the same or different, and where the solid support contains more than one target site, the target sites can be arranged in any pattern, including, for example, an array, in which the location of each target site is defined.

As used herein, the term "predetermined volume" is used to mean any desired volume of a liquid. For example, where it is desirable to perform a reaction in a 5 microliter volume, 5 microliters is the predetermined volume. Similarly, where it is desired to deposit 200 nanoliters at a target site, 200 nanoliters is the predetermined volume.

As used herein, the term "maintain a volume of a liquid" refers to a predetermined volume of the liquid and means that the volume of the liquid is kept within an acceptable amount of the predetermined volume An acceptable amount of a predetermined volume is an amount that is within 80% or more of the predetermined volume, generally within about 90% or more, and particularly about 95%, or about 98% or more of the predetermined volume.

As use herein, a volume of a liquid at a target site is maintained within a predetermined volume by dispensing an amount of liquid to the target site. In one embodiment, the amount of liquid dispensed to a target site is based on the evaporation rate of the liquid from the target site, such that the amount of liquid dispensed corresponds to the amount of liquid lost from the volume due to evaporation. As used herein, the term "corresponds," when used in reference to the amount of liquid being added to the reaction mixture ("amount added") and the amount of liquid that evaporates from the reaction mixture ("amount lost"), means that the amount added is, within an acceptable margin of error, equal to the amount lost. An acceptable margin of error is such that the amount added is within 20% or less of the amount lost, generally within about 10% or less, and particularly about 5% or less, or about 2% or less of the amount lost. An acceptable margin of error can be determined based, for example, on the susceptibility of a reaction to the effective concentration of one or more reactants in the reaction. In another embodiment, the disclosed systems and methods allow a predetermined amount of a liquid to be dispensed to a target site, for example, to initiate a reaction, to dilute a reaction, or to change the conditions of a reaction.

As used herein, the term "temperature controlling system" means a device for regulating the temperature of a solid support, particularly the temperature of a liquid present at a target site on a surface of the solid support. A temperature controlling system useful in an open system as disclosed can increase the temperature of a solid support, particularly a target site on the support, or decrease the temperature of the support, as desired. Temperature controlling systems are well known and readily available to those in the art, and are selected, in part, based on the range of temperatures desired, the physical characteristics of the solid support, and its facility of incorporation into a system as disclosed. A temperature controlling system can be, for example, an electrically or electromagnetically regulated heating element or heating/cooling element, such as a Peltier element, or a system that allows contacting the support with, for example, dry ice, liquid nitrogen, or a bath or stream of water maintained at a desired temperature.

As used herein, the term "interface" refers to a system for communicating an amount of liquid to be dispensed to a target site to maintain a predetermined volume. As such, an interface provides a means for controlling an amount of liquid dispensed from a liquid dispensing system. An interface can be in communication, either directly or indirectly, with the target site, with the liquid dispensing system, or with both.

As used herein, the abbreviations for amino acids and protective groups and other such abbreviations are in accord with their common usage and, if appropriate, the IUPAC-IUB Commission on Biochemical Nomenclature [see, (1972) *Biochem.* 11: 1726].

Systems

Systems are provided for performing a reaction in an unsealed environment. The disclosed systems and methods provide a means of maintaining a volume of a liquid, for example, a reaction mixture, present in an unsealed environment and, therefore, susceptible to loss of volume by evaporation. In general, the environment into which evaporation can occur is a volume of a gaseous medium, which can be, but need not be, substantially greater than the volume of liquid. A relatively large surface of the liquid can be in direct contact with the environment, and a substantial amount of a liquid can evaporate into the environment, for example, ten percent or more of the total volume, such that a substantial change in the effective concentration of reactants would occur if the amount of liquid lost due to evaporation is not replaced by a corresponding amount of the liquid dispensed to the volume.

In a system or method as disclosed herein, the liquid generally is present on a surface of a solid support, at a target site, and the environment into which evaporation can occur is air. Many liquids and reactants, including biopolymers, suitable for use in a disclosed system or method are susceptible, for example, to oxidation. Accordingly, an open system as disclosed herein can be placed in a vessel in which the environment can be controlled, for example, the environment can be gaseous medium such as nitrogen, an inert gas such as argon, or other gaseous medium. It should be recognized, therefore, that an unsealed environment may be isolated from the "open air," but nevertheless can be considered an "unsealed environment" for purposes of the present disclosure provided that a liquid, the volume of which is to be maintained, is in contact with a gaseous medium, into which the liquid can evaporate. Further in this regard, various reactions must be performed under conditions of low pressure or high pressure, where the rate of evaporation of a liquid is greater than or less than, respectively, the rate of evaporation of the liquid in open air. An open system as disclosed herein also can be used for performing such reactions, as well as reactions that contain evaporation suppressants or agents that alter the freezing point or boiling point of the liquid, particularly such agents that do not affect a reaction, or for performing reactions in the light, which can be any spectrum of light, or in the dark.

The disclosed systems and methods provide a means to maintain a volume of a liquid at a predetermined volume, where the volume otherwise would decrease below the predetermined volume due to evaporation. An open system can include a solid support having a target site, which can contain a volume of liquid; a liquid dispensing system, which can dispense a liquid to the target site; a temperature controlling system, which can regulate the temperature of the solid support; and an interface, which can indicate an amount of liquid to be dispensed from the liquid dispensing system. In an open system as disclosed herein, the amount of liquid dispensed from a liquid dispensing system can correspond to an amount of liquid lost by evaporation, or can be any predetermined amount of liquid.

The liquid present on a target site can be, for example, a solvent or other component of a reaction mixture. Other components of a reaction mixture can include a substrate, for example, a cell, a biopolymer or an organic or inorganic molecule, and the volume of the reaction can be any desired volume, particularly a submicroliter volume. An open system as disclosed herein can be particularly useful for synthesizing biopolymers such as polynucleotides, polypeptides, polysaccharides and the like, including for synthesizing combinatorial libraries of molecules such as biopolymers, and for performing biological reactions, or chemical reactions using a biopolymer as a substrate, in submicroliter volumes, without concern that evaporation of a liquid from the reaction mixture will undesirably affect the reaction, and, additionally, allows for performing such reactions as single tube reactions.

An open system also can contain a solid support having a target site; a liquid dispensing system, which can dispense a liquid to the target site; a temperature controlling system, which regulates the temperature of the solid support; and means for regulating an amount of liquid dispensed from the liquid dispensing system. Any means for regulating an amount of liquid dispensed from the liquid dispensing system can be used, including manual manipulation of the liquid dispensing system by an individual monitoring the system, or automatic control of the liquid dispensing system due to an interface between the liquid dispensing system and the temperature controlling device or a temperature sensing device in contact with the solid support.

Interface

An interface generally is a component of an automated or semi-automated open system for maintaining a volume of a liquid at a target site. In particular, an interface can be a computerized system that receives input relevant to the volume of a liquid at a target site and, based on that input, provides an instruction to the liquid dispensing system to dispense an amount of liquid that corresponds to an amount of liquid lost from the target site. Thus, an interface for regulating an amount of liquid dispensed by a liquid dispensing system can be, for example, a system for detecting the level of a meniscus, or a computer for receiving input of data from which the volume or level can be calculated. Thus, the interface can include a computer programmed with an appropriate algorithm or software for calculating such level.

Input relevant to the volume of a liquid at a target site can be obtained directly, for example, by detecting a decrease in the level of a meniscus of the liquid or the level of a drop of the liquid below a predetermined point. As disclosed herein, a liquid on a target site can be, for example, in a well or cylinder. In such a case, wherein the liquid is physically surrounded by a barrier, a meniscus forms in the liquid. In addition, a liquid can be placed as a drop on the target site, wherein the liquid is constrained, for example, by the physico-chemical characteristics of the target site. In either case, the level of the liquid can be monitored by detecting a decrease in the level of the meniscus or the drop of liquid.

A decrease in a meniscus below a predetermined point can be detected, for example, by including the liquid in a circuit. In such a system, when the meniscus falls below a predetermined point, which is the point required for the circuit to be complete, a change in the circuit is detected. The interface, upon receiving such input, can indicate that a volume of liquid is to be dispensed to the target site by the liquid dispensing system, until the circuit is reestablished, at which time dispensing of the liquid is terminated. Such a circuit conveniently can be constructed into a microchip using well known methods of photolithography and microelectronics.

Similarly, where the liquid on the target site has a meniscus or is in the form of a droplet, such input can be obtained by detecting a change in the diffraction, transmission or absorbance of photons as the volume of liquid decreases below a level defined by the positions of an appropriate light source and detector. A system using fiber optics can be useful for monitoring the level of a liquid on a target site and, conveniently, can be included in a detection system, if desired, to monitor the extent of a reaction. As well as the direct methods exemplified above, input relevant to the volume of a liquid at a target site also can be obtained indirectly, for example, using an algorithm that determines the rate of evaporation from the target site based on the temperature of the support containing the target site, the time the temperature has been maintained, and the vapor pressure of the liquid.

A computer with appropriate inputs and outputs, for example, can be used to monitor the temperature of the solid support and, based on various parameters, including, for example, the chemical nature of the liquid, the surface area of the liquid exposed to the environment, and the time the liquid is maintained at a particular temperature, can estimate the rate of evaporation of a liquid from the target site, and, through an interface, communicate an amount of liquid to be dispensed from the liquid dispensing system to the target site to maintain the liquid at a predetermined volume. For example, a means for regulating an amount of liquid dispensed to a target site can interface with a liquid dispensing system such as a nanoliter dispensing system to compensate for evaporation, thereby maintaining the volume of a liquid at a target site at a predetermined volume (see, e.g., FIG. 1). A computer can directly control the liquid dispensing system to dispense a desired volume, which corresponds to the amount of liquid that evaporates from the target site. The amount of evaporation will depend, in part, on the temperature of the target site, which can be on the surface of a microchip present in a holder that is integrated with , for example, a Peltier element, and a thermistor. The temperature of the support and, therefore, the liquid at a target site, can be any temperature, which can be adjusted based on input from the computer, which is interfaced with the temperature controlling system. Based on the temperature of the microchip, the computer can calculate a rate or amount of evaporation and signal the nanoliter dispensing system accordingly.

A temperature sensing device such as a thermistor produces a signal that indicates the temperature of the support, for example, a microchip support (see FIG. 1). The support temperature signal can be provided to the computer, directly or through the temperature controlling system. Based on the temperature of the support, programming in the computer determines the amount or rate of evaporation and, therefore, a volume of liquid that can be dispensed to the target site to maintain the volume of the liquid at a predetermined level. The computer can provide the temperature controlling system with a signal that indicates the temperature to which the support will be set. Upon receiving the temperature setting signal, the temperature controlling system produces a Peltier element control signal, which directs the Peltier element to adjust the support to the indicated temperature.

An interface need not be directly connected to or control the liquid dispensing system, but can be connected instead to a display, which indicates the amount of liquid needed to be dispensed to maintain the volume of the liquid at a predetermined volume. An individual then can manipulate the liquid dispensing system. In addition, the interface need not be directly connected to the solid support, but can be connected instead to the temperature controlling system and, based on the setting of the temperature controlling system, the chemical and physical nature of the solid support, and the time the temperature is applied to the support, can determine the temperature of the solid support and, therefore, the amount of liquid to be dispensed to the target site. The interface then can display the amount of liquid to be dispensed such that an individual can manipulate the liquid dispensing system, or can transmit the information to the liquid dispensing system, thereby automatically controlling the system.

An open system, as disclosed herein, also can contain means for containing a volume of a liquid; means for dispensing a liquid; means for controlling the temperature of the reaction volume containing means; and means for regulating an amount of liquid dispensed from the liquid dispensing means. A means for regulating an amount of liquid dispensed can include an interface, for example, a computer programmed with software for calculating the appropriate rate or amount. A computer can interface, for example, with the solid support, thereby monitoring the temperature of the support, and can indicate an amount of liquid to be dispensed to a target site to maintain a predetermined volume of the liquid. The computer can display the amount of liquid to be dispensed and an operator can manipulate the liquid dispensing system such that the amount of liquid is dispensed, or the computer can further interface with the liquid dispensing system, thereby causing the amount of liquid to be dispensed.

Solid Supports

A solid support useful in an open system for maintaining a volume of a liquid at a predetermined volume can be constructed of any material having a surface, which can be flat or geometrically altered, for example, to include wells. The solid support is any known to those of skill in the art as matrix for performing synthetic reactions and assays. It can be fabricated from silicon, glass, silicon-coated materials, metal, a composite, a polymeric material such as a plastic, a polymer-grafted material, such as a metal-grafted polymer, or other material as disclosed herein. This material can be further functionalized, as necessary, for example, chemically, to enhance or permit linkage of molecules or other particles, such as cells or cell membranes or viral envelopes or other such biological materials, of interest. The surface of a support can be modified, such as by radiation grafting of a suitable polymer on the surface and derivatization thereof to render it suitable for binding capturing a molecule or particle, such as a cell. The support may also include beads linked thereto (see, copending allowed U.S. application Ser. No. 08/746,036, copending U.S. application Ser. No. 08/933,792, and International application No. PCT/US97/20194, which claims priority to the U.S. applications). It may also include dendrite trees of captured material, or combinations of such additional components. A solid support can have one or more target sites, each of which can contain or retain a volume of a liquid.

By way of example, a solid support can be a flat surface such as a glass fiber filter, a glass surface, a silicon or silicon dioxide surface, a composite surface, or a metal surface, including a steel, gold, silver, aluminum or copper surface, a plastic material, including polyethylene, polypropylene, polyamide or polyvinylidenedifluoride, which further can be in the form of multiwell plate or a membrane; can be in the form of a bead (or other geometry) or particle, such as a silica gel, a controlled pore glass, a magnetic or cellulose bead, which can be in a pit of a flat surface such as a wafer, for example, a silicon wafer; or can be a pin, including an array of pins suitable for combinatorial synthesis or analysis (see, e.g., International PCT application No. WO98/20019), comb, microchip. The skilled artisan will recognize that various factors, including the size and shape of the support and the chemical and physical stability of the support to the conditions to which it will be exposed, will be considered in selecting a particular solid support for use in a disclosed system or method.

A solid support contains one or more target sites, which can contain a volume of a liquid. A target site can be, for example, a well, pit, channel, or other depression, with or without rims, on the surface of a solid support; can be a pin, bead or other material, which can be positioned on a surface of a solid support; or can be a physical barrier such as a cylinder, cone or other such barrier positioned on a surface of a solid support.

A target site also can be, for example, a reservoir or reaction chamber, which is attached to a solid support (see, for example, Walters et al., *Anal. Chem.* 70:5172–5176 (1998). In addition, a target site can be etched, for example, on a surface of a silicon wafer using a photolithographic method (see, for example, Woolley et al. (*Anal. Chem.* 68:4081–4086 (1996)). Photolithography allows the construction of very small target sites, including wells or towers, and, for example, has been used in combination with wet chemical-etching to construct "picoliter vials" on microchips (Clark et al. *CHEMTECH* 28:20–25 (1998)).

A support also can be a glass or silicon surface containing wells having a very thin base that is transparent to electromagnetic radiation of a desired wavelength, such as laser light, thereby permitting measurement of parameters, such as volume, or an excitation wavelength for fluorescence measurement.

A target site also can be defined by physico-chemical parameters such as hydrophilicity, hydrophobicity, the presence of acidic or basic groups, groups capable of forming a salt bridge, or any surface chemistry that allows a liquid to grow primarily in the z direction. For example, where the liquid to be placed on a target site is water or an aqueous solution, the target site can be defined by a hydrophilic area surrounded by a hydrophobic area on the surface of a solid support, or by a series of rows, alternately having less hydrophobic rows and more hydrophobic rows, whereby the aqueous mixture is constrained to the less hydrophobic rows. With respect to such a target site, the aqueous solution is dispensed, for example, onto the hydrophilic area, and is constrained from spreading from the target site due to the adjacent and surrounding hydrophobic area. Conversely, where the liquid is a nonpolar liquid, it is dispensed onto a hydrophobic region and is constrained in that region due to an adjacent hydrophilic region or a region or that is less hydrophobic that the region to which the liquid is applied.

A solid support can have a single target site, or can contain a number of target sites, for example, 2 sites, 10 sites, 16 sites, 100 sites, 144 sites, 384 sites, 1000 sites, or more, all or some of which can be the same or can be different. Where a solid support contains more than one target site and, therefore, can contain, for example, more than one reaction mixture, the characteristics that define each target site serve not only to constrain a reaction mixture, but also to prevent intermingling of different reaction mixtures or other liquids on the support. In addition, where a solid support contains more than one target site, the target sites can be arranged in any pattern, for example, in a line, a spiral, concentric circles, rows, or an array of rows and columns. Furthermore, the location of each target site of a number of target sites on a support can be defined. The availability of such addressable target sites on a solid support allows multiple reactions to be performed in parallel and is convenient, for example, for performing multiplex reactions, for including control reactions with test reactions such that all are performed under identical conditions, for performing a similar reaction under different conditions, or for performing different reactions.

Immobilization of a Reagent to a Solid Support

A substrate or other component of a reaction mixture can be immobilized to a solid support, particularly to a target site on the support, by a covalent interaction or a noncovalent interaction that is stable to the particular conditions of the reaction, as desired. A biopolymer, for example, can be immobilized directly to a solid support, or indirectly, for example, by immobilization to a spacer molecule, which is immobilized to the support. Furthermore, a spacer molecule can be a part of the biopolymer to be immobilized, or can be a separate molecule that directly or indirectly binds the biopolymer, for example, an oligonucleotide including a spacer nucleotide sequence and a sufficiently complementary probe or primer sequence, which can hybridize to a polynucleotide biopolymer.

Immobilization of a biopolymer can be mediated by a specific binding reaction, for example, by hybridization of a first nucleic acid molecule to a sufficiently complementary second nucleic acid, one of which is immobilized to the support. Similarly, immobilization can be through a first protein to a second protein, one of which is immobilized to the support, for example, an antibody and a polypeptide, which can be expressed on the surface of a cell, having an epitope recognized by the antibody; or an enzyme and its substrate; or any pair of proteins capable of homodimer or heterodimer formation. In addition, immobilization can be between a nucleic acid binding protein and a polynucleotide containing the sequence recognized by the binding protein.

A crosslinking agent also can be used to immobilize a substrate or other component of a reaction mixture to a solid support, through a reversible or irreversible linkage. A useful crosslinking agent can be any agent, including a homo-bifunctional or hetero-bifunctional agent, that is capable of reacting with a functional group present on a surface of the insoluble support and with a functional group present in the substrate or other component to be immobilized to the support. Useful bifunctional cross-linking agents include N-succinimidyl (4-iodacetyl) aminobenzoate (SIAB), dimaleimide, dithio-bis-nitrobenzoic acid (DTNB), N-succinimidyl-S-acetyl-thioacetate (SATA), N-succinimidyl-3-(2-pyridyidithiol propionate (SPDP), succinimidyl 4-(N-maleimidomethyl) cyclohexane-1-carboxylate (SMCC) and 6-hydrazinonicotimide (HYNIC) (see, also,, Wong "Chemistry of Protein Conjugation and Cross-Linking," (CRC Press 1991); Hermanson, "Bioconjugate Techniques" (Academic Press 1995)).

Immobilization of a substrate or other component of a reaction to a solid support can be particularly useful where the crosslink is mediated by a selectively cleavable linker, which can be cleaved under defined conditions. A biopolymer, for example, can be directly linked to a solid support via a reversible or irreversible bond between an appropriate functionality (L') on the biopolymer and an appropriate functionality (L) on the solid support, or on a molecule linked thereto, for example, a spacer molecule. Selectively cleavable linkers include photocleavable linkers and chemically cleavable linkers (see, e.g., International PCT application No. WO98/20019), and enzymatically cleavable linkers such as a polynucleotide sequence containing a particular restriction endonuclease site or a RNase digestion site or a polypeptide sequence containing a particular peptidase site.

Photocleavable linkers, which are cleaved upon exposure to light (Goldmacher et al., *Bioconj. Chem.* 3:104–107 (1992)), include a nitrobenzyl group as a photocleavable protective group for cysteine (Hazum et al., in *Pept. Proc. Eur. Pept. Symp.*, 16th (ed. K. Brunfeldt, 1981), pages 105–110); water soluble photocleavable copolymers, including hydroxypropylmethacrylamide copolymer, glycine copolymer, fluorescein copolymer and methylrhodamine copolymer (Yen et al., *Makromol. Chem* 190:69–82 (1989)); a cross-linker and reagent that undergoes photolytic degradation upon exposure to near UV light (350 nm; Goldmacher et al., *Bioconj. Chem.* 3:104–107 (1992); nitrobenzyloxycarbonyl chloride cross-linking agents (Senter et al., *Photochem. Photobiol* 42:231–237 (1985); and 3-amino-(2-nitrophenyl) propionic acid (Brown et al., *Molecular Diversity*, pages 4–12 (1995); Rothschild et al., *Nucl. Acids Res.* 24:361–66 (1996)). A photocleavable bond such as a charge transfer complex or a labile bond formed between relatively stable organic radicals can be useful, for example, where the sample is to be examined by mass spectrometry.

A linkage also can be formed with L' being a quaternary ammonium group. Where the sample is to be examined by mass spectrometry, the surface of the solid support also can carry a negative charge, which can repel, for example, a negatively charged nucleic acid backbone and facilitate desorption of a polynucleotide to be detected. Desorption can occur either by the heat created by the laser pulse or, depending on L', by specific absorption of laser energy, which is in resonance with the L' chromophore.

The L–L' chemistry can be a type of disulfide bond, which is chemically cleavable using mercaptoethanol or dithioerythrol; a biotin/streptavidin system; a heterobifunctional derivative of a trityl ether group that can be cleaved under mildly acidic conditions as well as under conditions of mass spectrometry (Köster et al., *Tetrahed. Lett.* 31:7095 (1990)); a levulinyl group cleavable under almost neutral conditions with a hydrazinium/acetate buffer; an arginine-arginine or lysine-lysine bond, which is cleavable by an endopeptidase enzyme such as trypsin; a pyrophosphate bond, which is cleavable by a pyrophosphatase; or a ribonucleotide bond in an oligodeoxynucleotide sequence, which can be cleaved by a ribonuclease or alkali. In addition to acid-labile trityl linkers, acid cleavable linkers include bis-maleimideothoxypropane; adipic acid dihydrazide linkers (Fattom et al., *Infect. Immun.* 60:584–589 (1992)); and acid labile transferrin conjugates that contain a sufficient portion of transferrin to permit entry into the intracellular transferrin cycling pathway (see, for example, Welhöner et al., *J. Biol. Chem.* 266:4309–4314 (1991)).

The L and L' functionalities also can form a charge transfer complex and thereby form a temporary L–L' linkage; a charge-transfer "band" can be determined by UV/vis spectrometry (R. Foster, "Organic Charge Transfer Complexes" (Academic Press 1969)), and the laser energy can be tuned to the corresponding energy of the charge-transfer wavelength so as to effect specific desorption of a sample for a solid support. A reversible L–' linkage also can be generated by homolytically forming relatively stable radicals, which, under the influence of a laser pulse, for example, during mass spectrometry, desorption and ionization occurs at the radical position. Those skilled in the art will recognize that other organic radicals can be selected and that, in relation to the dissociation energies needed to homolytically cleave the bond between them, a corresponding laser wavelength can be selected (C. Wentrup, "Reactive Molecules" (John Wiley & Sons 1984)).

Thiol-reactive functional groups are particularly useful for immobilizing a biopolymer to a solid support. Thiol-reactive functional groups react with a nucleophilic thiol moiety to produce a covalent bond, for example, a disulfide bond or thioether bond. In general, thiol groups are good nucleophiles, and preferred thiol-reactive functional groups are reactive electrophiles. Thiol-reactive functional groups are known in the art and include, for example, haloacetyls such as iodoacetyl; diazoketones; epoxy ketones; $\alpha,\beta$-unsaturated carbonyls such as $\alpha,\beta$-enones; and other reactive Michael acceptors, including maleimide, acid halides, benzyl halides, and the like.

A free thiol group present on a polypeptide or incorporated into a polynucleotide can react with a free thiol group such as an iodoacetyl-modified surface (or other thiol-reactive surface functionality) of the support through disulfide bond formation, thereby immobilizing the biopolymer to the support. In addition to being reversible, for example, by exposing the bond to reducing conditions, thiol reactive linkages also provide the advantage that reaction of a thiol group can be prevented temporarily by blocking with an appropriate protecting group (Greene and Wuts, in "Protective Groups in Organic Synthesis" 2nd ed. (John Wiley & Sons 1991)).

A polynucleotide can be modified at the 3'-terminus or 5'-terminus by reaction with a disulfide-containing modifying a reagent, or by enzymatically or non-enzymatically attaching a thiolated primer. A 5'-phosphoramidate functionality can also provide an attachment point for a thiol or disulfide-containing cytosine or deoxycytosine residue. A disulfide-modified nucleic acid can be reduced in a reaction using, for example, tris-(2-carboxyethyl)phosphine (TCEP), at a concentration of about 1 mM to 100 mM, preferably about 10 mM; a pH of about 3 to 6, preferably about pH 4.5; a temperature in the range of 20° C. to 45° C., preferably about 37° C.; and for a time period in the range of about 1 hour to 10 hours, preferably about 5 hours; or using dithiothreitol in a concentration of about 25 mM to 100 mM, depending on whether the reactant is isolated; at a pH in the range of 6 to 10, preferably about pH 8; at a temperature of about 25° C. to 45° C., preferably about 37° C.; and for a time of about 1 hour to 10 hours, preferably about 5 hours. Use of TCE provides an advantage in the low pH at which it is reactive, which effectively protonates thiols, thereby suppressing nucleophilic reactions of thiols and resulting in fewer side reactions than with other disulfide reducing agents used at higher pH ranges.

Temperature Controlling System

The temperature of a solid support having a target site is maintained using a temperature controlling system. An open system for maintaining a volume of a liquid at a predetermined volume can include a temperature controlling system, which can heat or cool a solid support, particularly a target site on the support, to a desired temperature. A temperature controlling system is selected, in part, based on the purpose for which the open system is to used, for example, the reactions to be performed using the open system. As such, a temperature controlling system can be selected that can cool a solid support, for example, to a temperature of 4° C. or less, or 0° C. or less, or –20° C. or less, or –80° C. or less, including, if desired, to about the temperature of dry ice, or liquid nitrogen, or liquid helium; or can heat a solid support, for example, to 25° C. or more, or 37° C. or more, or 45° C. or more, or 65° C. or more, or 90° C. or more, including, if desired, to temperatures greater than 100° C. A temperature controlling system that can heat or cool a solid support within a temperature range of about –20° C. to about 95° C. can be particularly useful as a component of an open system that is to be used for performing biological reactions or reactions involving biological materials, since the reaction volume, including the reactants can be maintained at a low temperature prior to initiating the reaction, then can be adjusted to the appropriate temperature or temperatures for performing the desired reaction.

A thermoelectric module can be particularly useful as a temperature controlling system in an open system as disclosed herein. A thermoelectric module is a solid state device that can be used as a heat pump, utilizing the Peltier effect, to move heat. Depending on the direction that module moves heat, it can be used to heat or cool a solid support. A single thermoelectric module generally can achieve a temperature difference of about 60° C. to 70° C., and several such modules can be used in combination to attain a temperature difference of up to 131° C. Furthermore, by reversing the direction of the current to the module, the direction heat is moved can be reversed. Thus, the thermoelectric module can be used to reversibly heat and cool a support and, therefore, a reaction mixture such as a PCR reaction located at a target site on the support. Thermoelectric modules are commercially available (Melcor, Trenton N.J.; Americool, Nashua N.H.).

A temperature controlling system such as the Peltier Thermal Cycler (PTC-200 DNA Engine; M. J. Research, Inc., Watertown Mass.) is an example of a temperature controlling system that can be integrated into an open system as disclosed herein. The PTC-200 DNA Engine utilizes a Peltier-Joule heat pump; has a temperature range of –5° C. to 105° C.; provides temperature homogeneity of samples within 30 seconds of reaching 90° C.; accepts a variety of sample supports, including microscope slides and multi-well plates; and conveniently can be interfaced with a computer. An LFI-3526 system, which contains a 22W Peltier element controlled by a programmable thermoelectric temperature controller (Wavelength Electronic, Inc., Bozeman Mont.; see Example 1), is another example of a temperature controlling system useful in an open system as disclosed.

An electronic temperature controlling system also can be incorporated into an open system as disclosed (see Burns et al., *Proc. Natl. Acad. Sci. USA* 93:5556–5561 (1996)). An electronic temperature controlling system can be conveniently constructed, for example, in a microchip using well known methods (see, for example, Woolley et al. *Anal. Chem.* 68:4081–4086 (1996)). Such an electronic temperature controlling system allows thermal cycling using a pulsed width modifier and, therefore, can be useful, for example, for performing PCR reactions (Woolley et al. (*Anal. Chem.* 68:4081–4086 (1996); see, also, Ross et al., *Anal. Chem.* 70:2067–2073 (1998); Belgrader et al., *Clin. Chem.* 44:2191–2194 (1998)).

A temperature controlling system also can include a temperature measuring system, which can be used to determine the temperature of a solid support, particularly of a liquid present at a target site on the surface of the support. A temperature measuring system can be, for example, a thermocouple, thermometer, or the like, which can be in contact with a liquid on the support and, therefore, directly determine the temperature of the liquid, or can be in contact with the solid support, thereby providing an indication of the temperature of the liquid. A temperature also can be, for example, an infrared detector, which can monitor the temperature of a liquid at a target site without contacting the support. The use of thermocouples can be particularly convenient because they can be very small in size and can be constructed, for example, into microchips (see Woolley et al. (*Anal. Chem.* 68:4081–4086 (1996)). A thermocouple can be in direct contact with a target site, including with a reaction volume at each target site in an array on a solid support, thereby allowing precise monitoring of the temperature of each reaction simultaneously. Input from such thermocouples can be incorporated into an algorithm that allows a calculation of the evaporation rate of liquid from each reaction mixture in an array, and, through the appropriate interface, indicates an amount of liquid to be dispensed to each target site that corresponds to the amount that evaporates from a reaction mixture. Such a means for monitoring the temperature of a number of reaction volumes simultaneously can be particularly useful since different reactions may be being performed at different sites in the array, or because the rate of heating or cooling of different reaction mixtures on a solid support are not identical due, for example, to inhomogeneities in the support or to different concentrations of reagents in a mixture.

The temperature generated by the temperature controlling system and, therefore, the temperature of the solid support, also can be determined based on the particular setting of the temperature controlling system, the physical nature of the solid support, and the time the temperature is applied to the support. Such temperatures can be calculated based on known parameters, or can be determined empirically by heating or cooling a support for incremental periods of time, at incremental temperatures, and measuring the temperature of the support accordingly.

Liquid Dispensing/Removing Systems

Dispensing

A liquid dispensing system can be an active apparatus, which can be a mechanical, electrical, pressure or pneumatic driven liquid dispensing system, for example, a piezo electric pipette driven by mechanical pressure; or can be a passive apparatus, which contains a reservoir. In addition, a liquid dispensing system can contain a heating element, for example, microresistors, which provides the ability to maintain a liquid in the system at a desired temperature, for example, at or near a reaction temperature.

A liquid dispensing system can include a single fluid transmitting vesicle or multiple vesicles, which can be manipulated independently or together in parallel. A fluid transmitting vesicle can be a solid vesicle, to which the liquid can adsorb and be transferred, or can have a bore, through which the liquid is transferred. Thus, a fluid transmitting vesicle can be a pipet, particularly a micropipet, which contains a chamber for holding or transferring the liquid and an end from which the liquid can be dispensed to a target site; a pin tool, which can have a bore, or can be solid vesicle, which, when dipped into a chamber holding a liquid, adsorbs a volume of the liquid, which then can be transferred to a target site; or a liquid sonicating, vaporizing or ink jet device, which contains a chamber for holding the liquid, and an end from which the liquid is dispensed in droplets, the volume and rate of dispensing of which can be adjusted as desired. A fluid transmitting vesicle can be formed of a metal, composite, glass, silica, or polymeric material, or any other suitable material. A nanoliter liquid dispensing system such as a nanoliter pipet can be particularly useful in a system as disclosed. Nanoliter dispensing systems are provided, for example, in copending allowed U.S. application Ser. No. 08/787,639, U.S. application Ser. No. 08/786, 988, and International PCT application No. WO 98/20166, which claims priority to the U.S. applications.

A liquid dispensing system can be part of a liquid handling system, which can contain, in addition to the liquid dispensing system, a chamber for holding a liquid to be dispensed. Such a chamber can be used to directly provide the liquid dispensing system with the appropriate liquid to be dispensed, or can be connected to the liquid dispensing system by a conduit, which mediates transfer of the liquid from the holding chamber to the dispensing system. A conduit can be any suitable conduit, for example, plastic or stainless steel tubing, and can be particularly useful if it can be sterilized without impairing its function. Where it is desirable to dispense a liquid to a target site at a particular temperature, the liquid dispensing system, as discussed above, or a component of a liquid handling system can be maintained at the particular temperature such that the liquid is dispensed at the desired temperature. An advantage of a liquid handling system is that it can contain more than one holding chamber and, therefore, can conveniently allow more than one liquid to be dispensed from a single liquid dispensing system, for example, from a pin having a bore, without a need to change the position of the liquid dispensing system with respect to the target site. Such a system is particularly convenient where the fluid transmitting vesicle, for example, a pin tool, has n array of fluid transmitting vesicles, which are positioned with respect to a corresponding array of target sites on a solid support.

A liquid dispensing system allows an amount of liquid, preferably a controlled amount, to be dispensed to a target site. The liquid can be dispensed as a continuous stream, or as droplets, which can be dispensed continuously or in a burst mode. The amount of liquid dispensed can be any amount, as desired, including a submicroliter amount or less, and can be dispensed for the purpose of maintaining a liquid at a predetermined volume, or for initiating, terminating or changing the conditions of a reaction at the target site.

A liquid dispensing system can dispense one or more liquids to a single target site, or can dispense one or more liquids serially or in parallel to multiple target sites, which can be in an array. A liquid dispensing system useful for dispensing a predetermined amount of a liquid in parallel can include, for example, an assembly of liquid transmitting systems such as pins, each of which can have a narrow interior chamber suitable for holding a volume of the liquid to be dispensed (see, for example, International PCT application No. WO98/20166). The pins can be fit inside a housing, which can have an interior chamber connected, for example, to a pressure source that regulates the flow of liquid through a pin, thereby allowing controlled dispensing of a predetermined volume of the liquid. Alternatively, the liquid dispensing system can include a jet assembly and a transducer element mounted to a pin, and can dispense an amount of liquid to a target site by spraying the liquid from the pin, or by allowing a drop of the liquid to form on the tip of the pin, where it can be contacted to the target site and dispensed.

A liquid dispensing system can include a single chamber for holding a liquid and, therefore, allow a single liquid to be dispensed, or can contain several chambers, each of which can hold a different liquid and variably can be in connection with the fluid transmitting vesicle. As such, a liquid dispensing system can include a selection element having, for example, a pressure source or a piezoelectric element coupled to a liquid holding chamber and in communication with the fluid dispensing vesicle such that, at a selected pressure condition or a selected voltage, a particular liquid is dispensed at a predetermined amount. Such a selection element conveniently can be interfaced with and controlled by a computer algorithm, which can be monitoring a rate of evaporation of a liquid from a target site, and can allow one or more liquids to be dispensed to a target site, or serially or in parallel to a plurality of target sites. In addition, a liquid dispensing system can dispense a liquid at any desired temperature, particularly the temperature at which a reaction is performed, or a temperature such as about 4° C., which, for example, can suspend a biological reaction. A nanoliter dispensing device, such as the NANO-PLOTTER NP1c (sold by GeSim; Dresden Germany) is an example of a liquid dispensing system that can be incorporated into an open system as disclosed (see Examples 1 and 2). The Nano-Plotter is a modular device that can be combined in a variety of ways depending upon the intended application. It is designed to spot microdroplets arrays onto flat substrates or microwell plates. The device as sold contains from one to eight micropipettes. For use herein, the device can be modified by including heating/cooling elements or heating means to heat the reservoir or the micropipetter or other portions thereof, preferably the surface of the target support, to heat or cool the liquid or surface prior to dispensing liquid to avoid a temperature gradient or change upon addition of liquid to a reaction mixture. Other nanoliter dispensing devices can also be used or adapted for use in these systems (see, e.g., copending allowed U.S. application Ser. No. 08/787,639, U.S. application Ser. No. 08/786,988, and International PCT application No. WO 98/20166, which claims priority to the U.S. applications, which describe nanoliter dispensing devices and systems).

The liquid dispensing system can dispense a liquid, which generally is reagent grade or better, or can dispense a solution containing the liquid. For example, in one aspect, the methods as disclosed provide diagnostic assays, the results of which can be analyzed using, for example, mass spectrometry, capillary electrophoresis, a charge coupled device, or a fiber optic system. Where a method such as MALDI-TOF mass spectrometry is used to analyze a component of a reaction, the sample to be analyzed is mixed with an appropriate matrix material (see, for example, U.S. Pat. No. 5,605,798; International PCT application No. WO96/29431; International PCT application No. WO98/20019). As such, a liquid dispensing system can be used to dispense a matrix solution to a target site, prior to subjecting the sample at the target site to mass spectrometry.

Liquid Removing

An open system as disclosed herein also can include a device for removing a liquid, which can be a reaction mixture, from a target site and transferring it to another target site or to a chamber for disposal. Such a device provides a convenient means to terminate a reaction, change the reaction conditions, wash a sample, or the like. Accordingly, in an embodiment, the liquid dispensing system also can function to remove a liquid from a target site. The liquid dispensing system, or independent device, can remove a liquid from a target site by contacting the fluid transmitting vesicle to the liquid to be removed and, for example, allowing capillary action to draw the liquid into the vesicle or applying a negative pressure to the vesicle. The removed liquid can be transferred to another location, which can be another target site or a chamber for disposal, and the fluid transmitting vesicle can be washed, if desired, and positioned for further use. A device for removing a liquid from a target site also can be a device that facilitates evaporation of the liquid from the target site, for example, a fan or other device for passing a stream of air or other gas over the liquid.

Regulation of Liquid Dispensing System

The liquid dispensing system is regulated so as to dispense a defined amount of a liquid to a target site. The amount of liquid dispensed can correspond to an amount of liquid lost due to evaporation or can be any desired amount of liquid, including a reaction mixture or a solution containing components of a reaction mixture. The liquid dispensing system can be regulated manually or can be regulated semi-automatically or automatically based, for example, on instructions from a computer or other signal transmitting system, which can be interfaced with the temperature controlling system (or a temperature sensing device), with the liquid dispensing system, or with the temperature controlling system (or temperature sensing device) and the liquid dispensing system.

A signal transmitting system can be any system that indicates an amount of liquid to be dispensed. For example, where the amount of liquid to be dispensed corresponds to an amount of liquid lost from a target site due to evaporation, the signal transmitting system can be any system that provides an indication of the amount of liquid lost. The amount of a liquid lost from a volume in an unsealed environment depends on the vapor pressure of the liquid, which is a function, in part, of the temperature; the surface area of the liquid exposed to the environment; the nature of the environment, including, for example, its relative humidity; and the time during which liquid can be lost. Since these parameters will be known or are determinable for a particular set of conditions, tables can be constructed for predicting an amount of a particular liquid that will be lost in a period of time from a known volume of the liquid applied to a particular target site at a known temperature. Accordingly, for purposes of the present disclosure, such a table is considered a signal transmitting system because an individual, monitoring the temperature and time of a particular reaction, can manipulate the liquid dispensing system to dispense an amount of liquid as indicated by the table.

For semi-automatic or automatic regulation of the liquid dispensing system, the signal transmitting system can be a conventional digital data processing system, for example, an IBM PC compatible computer system, an Apple computer or a UNIX based system, that is suitable for processing data and for executing program instructions that will provide information that can be communicated to the liquid dispensing system. Such a signal transmitting system can be any type of system suitable for processing a program of instructions that will operate the liquid dispensing system, although the system need not necessarily be programmable and can be a single board computer having a firmware memory for storing instructions relevant to regulating the liquid dispensing system.

A signal transmitting system can monitor the temperature of a solid support containing a target site directly, for example, by interfacing with a temperature sensing device, or indirectly, for example, based on the setting of the temperature controlling device and information relating to the chemical and physical nature of the solid support. Alternatively, or in addition, the signal transmitting system can be interfaced with the liquid dispensing system. For example, for semi-automatic operation, the signal transmitting system can be interfaced with either the liquid dispensing system or the temperature controlling system, and the component of the system that is not interfaced with the signal transmitting system can be operated manually by an individual. More conveniently, however, the temperature controlling system and the liquid dispensing system are interfaced with the signal transmitting system, and the entire system is operated automatically.

A signal transmitting system also can interface directly with the target site, including directly with the liquid. For example, a signal transmitting system can include a circuit in a microchip, where the circuit is interrupted by a well in the chip. Upon dispensing a liquid into such a well, the liquid can complete the circuit. In particular, the volume of liquid required to complete the circuit is indicative of the predetermined volume, which is to be maintained. Accordingly, where evaporation of the liquid occurs to the point that the level of the liquid decreases below the level required to maintain the circuit, an indication is provided that a liquid is to be dispensed to the target site. Upon dispensing a sufficient volume of the liquid such that the circuit is reestablished, dispensing of the liquid is terminated.

A signal transmitting system also can include a microbalance, which can detect minute changes in the weight of a support due to evaporation of a liquid from the surface of the support. In addition, a signal transmitting system can include a light source, which can be of any desired wavelength, and a detector appropriate for the light source. The light can be provided to a target site, for example, using a fiber optic, and the amount of diffraction of the light, or the transmission or absorption of photons can be monitored. A change in the amount of such a parameter can indicate, similarly to the circuit system discussed above, that the level of the liquid has decreased below a predetermined value, or, as discussed below, that an undesirable amount of evaporation has occurred. Such information then can be communicated such that an amount of liquid is dispensed to the target site that corresponds to the amount that has evaporated, thereby maintaining the volume of the liquid at a predetermined level.

A spectrophotometric detector system, for example, can include a laser, which can be a helium-argon laser, a helium-neon laser, an ultraviolet laser, or a laser that emits green or blue light, or can be a light emitting diode (LED), for example, a blue or a green LED. Such a detector system can be particularly useful where the support is a glass or silicon chip, which has wells or the like having a base that allows transmission of the particular wavelength of light. Using such a support, the light can be transmitted from below the chip, through the sample, and can be detected by a detector placed above the well. The light transmitting system and detector can be a single source, or can be arranged in an array that corresponds to positions of the target sites on the support. Furthermore, such a spectrophotometric system can be separate from the open system for maintaining a volume of a liquid in an unsealed environment, and the support can be repositioned to the detector system when desired. Preferably, however, the spectrophotometric system is integrated into the open system, thus allowing online monitoring of a reaction. In such an integrated system, a temperature controlling system such as a Peltier element is constructed with holes at positions corresponding to the target sites, particularly to the position at which the light source transmits the light to the support.

The use of a spectrophotometric system can allow monitoring of a reaction, for example, where the reactants are labeled with an appropriate fluorescent, luminescent or chemiluminescent moiety, for example, a reaction performed using the TaqMan™ assay (see Example 1). The light transmitting system and detector are selected based on the particular wavelength of light desired. Such a spectrophotometric system also is useful for monitoring the volume of a liquid at a target site, as disclosed above, for example, by detecting a change in the diffraction, transmission or absorbance of photons that reach the detector. Depending on the particular liquid at the target site, including the desired predetermined volume to be maintained, the reactants, when present, in the liquid, and the like, tables can be constructed that indicate, for example, the amount of light transmitted to a detector that signals an undesirable amount of evaporation of the liquid, such that a liquid dispensing system dispenses an amount of liquid that corresponds to the amount that evaporated.

Detection Systems

A reaction mixture, including a component added to the mixture, for example, a substrate, or an intermediate or product produced by the reaction, can be monitored using any detection system appropriate for the material being examined. The detection system is selected based in the particular material to be detected, and can be matched with a particular label where the material to be detected based on identifying the presence of a label attached to the material. Since the disclosed systems and methods are particularly useful for performing reactions in small volumes, particularly submicroliter volumes, the material to be detected generally is present in only a very small amount. Accordingly, the detection system is selected, in part, on its sensitivity for detecting the material.

A detection system can be a photometric or spectrophotometric system, which can detect ultraviolet, visible or infrared light, including fluorescence or chemiluminescence; a radiation detection system; a spectroscopic system such as nuclear magnetic resonance spectroscopy, mass spectrometry or surface enhanced Raman spectrometry; a charge coupled device; a system such as gel or capillary electrophoresis or gel exclusion chromatography; or other detection system known in the art, or combinations thereof.

A mass spectrometry detection system can be useful in an open system as disclosed because it can detect the presence of very small amounts of a material, for example, a biopolymer, and, at the same time provides an indication of the identity of the detected material. In addition, mass spectrometry does not require labelling a material to be detected, although the materials can be "labeled," for example, by incorporating mass differentiating functional groups into the materials where a multiplex reaction is to be performed. Mass spectrometry also is useful because the systems and methods disclosed herein can utilize a solid support such as a microchip, which can be introduced conveniently into the mass spectrometer.

A useful mass spectrometry detection system can be any of various formats, including ionization (I) techniques such as matrix assisted laser desorption (MALDI), continuous or pulsed electrospray (ESI), ionspray, thermospray, or massive cluster impact (MCI). Such ion sources can be matched conveniently with a detection format, including linear or reflectron time-of-flight (TOF), single or multiple quadruple, single or multiple magnetic sector, Fourier transform ion cyclotron resonance (FTICR), ion trap, and combinations thereof to yield a hybrid detector, for example, ion-trap/time-of-flight. For ionization, numerous matrix/wavelength combinations (MALDI) or solvent combinations (ESI) can be employed. MALDI-TOF mass spectrometry, including delayed extraction MALDI-TOF mass spectrometry is particularly useful as a detection system (see, for example, International PCT application No. WO98/20019;see, also, Whittal et al., *Anal. Chem.* 70:5344–5347 (1998), describing the use of MALDI-TOF mass spectrometry for the analysis of proteins isolated from single cells).

A charge coupled device (CCD) camera can be useful for detecting and imaging fluorescent, chemiluminescent or radionuclide labeled materials. Such a detection system has been adapted to analysis of reactions on microchips, and can allow the detection of thousands of binding reactions performed on a microchip (see Eggers and Ehrlich, *Hematol. Pathol.* 9:1–15 (1995); see, also, Eggers et al., *Biotechniques* 17:516–525 (1994). Using a CCD detecting system, biopolymers, which can bind an appropriately labeled material, or reagents that can bind an appropriately labeled material such as a fluorescently labeled biopolymer, are immobilized directly on the pixels of a CCD, and, following a reaction as desired, bound labeled materials are detected at the specific pixel location. The signal obtained from a CCD can be displayed, if desired, and can allow a quantitative determination, for example, of binding events. Furthermore, since the signal obtained using a CCD detector is received in real time, the signal can be used as an indication of the extent of a reaction, and can be interfaced with the liquid dispensing system to cause an amount of a liquid to be dispensed, for example, to terminate the reaction, or to change the conditions of the reaction such that a second reaction can be performed at the particular target site.

Where a substrate, or a product of a reaction to be detected, is labeled using, for example, a luminescent, fluorescent or chemiluminescent label, a fiber optic system can be used as a detection system (see, for example, Clark et al. CHEMTECH 28:20–25 (1998)). Fiber optics are particularly useful because their small size permits the monitoring of individual target sites, for example, in an array of target sites on a microchip. In addition, a fiber optic system can provide the additional function of monitoring the level of a liquid, as disclosed above. Other detection systems including laser scanners (Cheung et al., Nature Genet. 21:1519 (1999), capillary electrophoresis (Hadd et al., Anal. Chem. 69:3407–3412 (1997), and epifluorescence microscopy (Fodor et al., Science 251:767773 (1991) have been adapted to microchip devices and glass slides and can be used in an open system as disclosed herein.

Methods

Methods for maintaining a volume of a liquid in an unsealed environment also are provided. Such a method can be performed in an open system, for example, by determining the temperature of a solid support, having a target site, which can contain the volume of liquid; and, based on the temperature, dispensing at the target site an amount of liquid required to maintain the volume of the liquid. The amount of liquid to be dispensed can be determined, for example, using a computer algorithm that can calculate, based on various parameters, including the temperature of the support, the chemical nature of the liquid, and the volume to be maintained, the amount of liquid that evaporates from the site, such that the amount of liquid dispensed corresponds to the amount of liquid that evaporates. Alternatively, the volume can be monitored, for example, by a microscopic examination, using an appropriate optical system, or by a video imaging technique, such that, as the volume of a liquid at a target site decreases, liquid can be dispensed to maintain the volume within acceptable parameters. In another embodiment, the volume can be monitored by tracking the meniscus of the liquid and determining when the meniscus decreases below a defined point. Such monitoring can be performed by detecting a change in a circuit due to a decrease in the amount of liquid below a level required to maintain the circuit, or by a change in the quality of light being transmitted into the liquid.

Methods for performing a reaction in an unsealed environment also are provided. Such a method can be performed, for example, by determining the temperature of a solid support, which includes a target site containing a volume of the reaction mixture; and dispensing into the reaction mixture an amount of liquid required to maintain the volume. Such a method is particularly useful where the reaction mixture has a volume of a few microliters or less, generally a volume of about 20 microliters or less, and particularly about 500 nanoliters or less. The disclosed methods also are useful for performing submicroliter reactions at temperatures where the vapor pressure of a liquid in the reaction mixture is undesirably high, for example, about 2.5 kilopascals (kPa) or greater, particularly about 5 kPa or greater, or about 10 kPa or greater, such that evaporation of the liquid can substantially change the volume of the reaction mixture and adversely affect the reaction.

The disclosed methods are useful, for example, for performing a reaction in an aqueous environment at a temperature greater than about 22° C. (room temperature; RT; 72° F.), particularly at a temperature about 37° C. or greater, where the vapor pressure for water is 2.6447 kPa at 22° C., 6.2795 kPa at 37° C., and 84.529 kPa at 95° C. ("Handbook of Chemistry and Physics" 75th ed. (CRC Press, Inc., 1994); see pages 6-15 to 6-17; see, also, 6-77 to 6-108; and 15-43 to 15-49). As such, the disclosed methods can be used, for example, to perform various chemical, physical and biological reactions such as synthesis of a combinatorial library, a mammalian cell transfection, or a polymerase chain reaction.

A method for maintaining a volume, particularly a submicroliter volume, of a reaction mixture on a solid support in an unsealed environment can be performed by determining the rate of evaporation of a liquid from the reaction mixture; and dispensing into the reaction mixture an amount of liquid that corresponds to the amount of liquid that evaporates, thereby maintaining the volume of the reaction mixture.

Such a method can be useful, for example, where the reaction mixture contains a biopolymer, which can be a substrate or a product of the reaction. Following a reaction using a method as disclosed herein, the biopolymer or products of the biopolymer can be detected, either directly or indirectly. As such, the disclosed methods are useful for determining the sequence of a biopolymer, for synthesizing a biopolymer from monomeric subunits, and for detecting the presence of a particular biopolymer, for example, in a biological sample. Various methods for detecting a biopolymer are exemplified herein and other methods, which are selected based, in part, on the particular type of biopolymer, are well known to those in the art.

A method as disclosed herein can be useful for essentially any type of reaction, including, for example, where the substrate is a biopolymer, a biological reaction such as an enzyme-mediated polymerization, ligation, cloning, or a degradation reaction; a physical reaction such as a nucleic acid hybridization, the binding of a nucleic acid regulatory element by a particular nucleic acid binding polypeptide, or homodimerization or heterodimerization of polypeptides; or a chemical reaction such as a chemical labeling reaction, chemical synthesis of the biopolymer; or a chemical cleavage of the biopolymer, for example, cyanogen bromide cleavage of a polypeptide at a methionine residue or dimethylsulfate cleavage of a carbohydrate end group. The reaction also can be a chemical synthesis reaction, for example, synthesis of a combinatorial library of small molecules or of biopolymers; or can be a hydrolysis reaction such as a polysaccharide hydrolysis reaction.

A method as disclosed herein also is useful for a reaction involving a living cell. For example, the reaction can be a method of introducing a recombinant nucleic acid molecule, which can be contained in a vector, into a host cell in order to produce copies of the recombinant nucleic acid molecule or to express a polypeptide encoded thereby. Such a polypeptide can be isolated, if desired, or can be expressed for the purpose of providing an advantage to the cell expressing the polypeptide. The reaction also can involve contacting a cell with a physical, chemical or biological agent in order to identify a change in gene expression in the cell, for example, by imposing a heat shock on the cells, or by contacting the cells with a putative medicament. An open system as disclosed herein is useful for such reactions because it allows precise control of the reaction conditions, particularly the ability to maintain the reaction at a predetermined volume. Furthermore, because the reactions can be performed in very small volumes, studies involving only one or a few cells can be performed (see, for example, Clark et al. CHEMTECH 28:20–25 (1998)).

Sequencing Reactions

The methods disclosed herein can be used for a biopolymer sequencing reaction. For example, the biopolymer can be a polynucleotide, which can be sequenced using the Maxam-Gilbert chemical cleavage method, or an enzymatic reaction such as the Sanger-Coulson chain termination method or an exonuclease cleavage method. A biopolymer sequencing reaction such as the Maxam-Gilbert method or Sanger-Coulson method conveniently can be performed, for example, on a microchip, in which a number of reactions, including the four (or five) base specific reaction, can be performed in parallel on one or more polynucleotides, or a single base reaction can be performed on a number of different polynucleotide sequences. Such methods of polynucleotide sequencing result in the production of nested fragments of the polynucleotide, which can be detected using various methods, particularly mass spectrometry, including matrix-assisted laser desorption/ionization time-of-flight (MALDI-TOF) mass spectrometry or capillary electrophoresis.

In a chain termination sequencing reaction, for example, each reaction mixture is an aqueous solution, containing a polymerase, four nucleoside triphosphates, and a chain terminating nucleoside triphosphate; the water in the reaction mixture is susceptible to evaporation during the reaction, which generally is performed at a temperature of about 37° C. Particularly where the reaction is performed in a submicroliter volume on a solid support in an unsealed environment, the water can evaporate almost completely in a short period of time and, even where the reaction mixture does not evaporate to dryness, the loss of water volume can substantially alter the kinetics of the polymerase reaction, including the fidelity of nucleotide incorporation, and produce spurious results. A method as disclosed herein avoids such a problem by dispensing into the reaction mixture an amount of water that corresponds to the amount of water that evaporates during the reaction.

In the Maxam-Gilbert sequencing method, four or five separate reactions can be performed, each of which is performed under different conditions, with different liquids, including water, dimethyl sulfate, piperidine, and hydrazine (see Sambrook et al., "Molecular Cloning: A laboratory manual" 2nd ed. (Cold Spring Harbor Laboratory Press 1989), pages 13.11–13.13). For example, a sugar-phosphate cleavage reaction of the modified bases is performed using 1 M piperidine in water at 90° C. (vapor pressure of piperidine=84.1 kPa at 100° C.; and of water=101 kPa at 100° C.). As such, a method as disclosed herein, can be used to monitor the evaporation of piperidine and of water during the sugar-phosphate cleavage reaction and can allow an amount of each liquid to be dispensed to the target site during the reaction. The relative amount of each such liquid to be dispensed can be calculated, for example, based on the concentration of each liquid in the reaction and the vapor pressures of the liquids.

A polynucleotide also can be sequenced by an exonuclease reaction using a method as disclosed herein. For example, a multiplex exonuclease sequencing reaction can be performed on polynucleotides as disclosed in U.S. Pat. No. 5,622,824 and U.S. Pat. No. 5,851,765, wherein mass differentiated nucleic acid molecules containing mass modified nucleotides are prepared, immobilized to a target site, and contacted with an exonuclease. A number of exonuclease sequencing reactions can be run in parallel, for example, on a microchip, and the concentration of exonuclease, pH, and time of incubation can be varied in the different reaction mixtures to produce a desired range of degradation products. Time of incubation can be adjusted, for example, by maintaining the temperature of each target site at 4° C., then at predetermined times, adjusting the temperature of one or more target site to 37° C. The volume of each reaction mixture is maintained at a predetermined volume throughout the procedure. At the appropriate time, all of the reactions are terminated, for example, by removing the liquid and dissolved reagents from the target sites. The immobilized, exonuclease degraded mass differentiated nucleic acid molecules remain immobilized to the chip and are available for detection, for example, by mass spectrometry.

A polypeptide also can be sequenced using a chemical degradation method, for example, the Edman degradation method, which utilizes phenylisothiocyanate to sequentially cleave amino acids from the amino terminus of a polypeptide, or an enzymatic degradation reaction using an exopeptidase such as a carboxypeptidase, which sequentially cleaves amino acids from the carboxy terminus of a polypeptide, or an aminopeptidase, which sequentially cleaves amino acids from the amino terminus of a polypeptide.

The sequentially released amino acids or nested fragments of the polypeptide can be detected. Nested fragments of a polypeptide can be produced conveniently by performing a number of reactions in parallel on a microchip, where the polypeptides are reversibly immobilized to the solid support using, for example, photocleavable linkers, chemically cleavable linkers, or the like. After the reactions are complete and the immobilized fragments have been washed, they can be detected in situ, or can be released from the support for detection.

The methods as disclosed herein also can be useful for reactions in which a biopolymer is cleaved into smaller, but not necessarily monomeric, fragments. For example, a polynucleotide can be cleaved, partially or completely, using a restriction endonuclease or base specific endonuclease such as various RNA endonucleases. Similarly, a polypeptide can be cleaved into fragments using, for example, cyanogen bromide, which cleaves at methionine residues, or any of various endopeptidases such as trypsin and chymotrypsin. The fragments produced then can be detected to facilitate determining the order of the fragments within the larger polynucleotide or polypeptide. The methods disclosed herein also are applicable where the biopolymer is a carbohydrate, glycoprotein, proteoglycan or lipid, which is to be sequenced.

Synthesis Reactions

The disclosed methods for maintaining a volume, particularly a submicroliter volume, of a reaction mixture also are useful for a biopolymer synthesis reaction. For example, the biopolymer can be a polynucleotide, and the synthesis reaction can be a chemical synthesis reaction or an enzymatic synthesis reaction using a polymerase (see, for example, S. M. Hecht, ed. "Bioorganic Chemistry: Nucleic acids" (Oxford Univ. Press 1996)). Chemical synthesis of a polynucleotide can be performed using any of various methods, including the phosphotriester, phosphoamidate and H-phosphonate method (Hecht, ed. "Bioorganic Chemistry: Nucleic acids" Oxford Univ. Press 1996, pages 36–74), and utilizes various organic solvents, including, for example, acetonitrile, which has a vapor pressure of about 11.8 kPa at 25° C. and, therefore, is more susceptible to evaporation than water. As such, the disclosed methods are particularly useful for chemical polynucleotide synthesis reactions, since the volume of the reaction mixtures can be maintained at a predetermined volume throughout the reaction period.

An enzymatic synthesis reaction, in comparison, is performed in an aqueous solution. The biopolymer can be a ribonucleic acid, and the polymerase can be an RNA dependent RNA polymerase or an RNA dependent DNA polymerase. Where the polymerase is an RNA dependent DNA polymerase, the enzymatic synthesis reaction also can include a DNA dependent DNA polymerase, for example, a reverse transcriptionpolymerase chain reaction (RT-PCR).

A polynucleotide can be synthesized, for example, by PCR. In addition to the substrate polynucleotide and a polymerase, which can be a DNA polymerase or RNA polymerase, other components of a PCR reaction include nucleoside triphosphates, which can be deoxyribonucleotides, ribonucleotides or analogs thereof, and a set of primers, including a forward primer and a reverse primer. Nested PCR reactions also can be performed, in which case a second set of primers, which specifically hybridize to the first amplification product, are a component of the reaction. A primer can be any oligonucleotide, including an oligonucleotide containing oligonucleotide mimetics, such as PNA (protein nucleic acid formed by conjugating bases to an amino acid backbone, which render the base sequence less susceptible to enzymatic degradation; see, e.g., Nielsen et al. (1991) *Science* 254:1497), portion(s), provided that the nucleotide at the 3' end of such a primer is linked to the oligonucleotide by a phosphodiester bond, or the like, such that extension of the primer from the 3' end can occur. The disclosed methods of maintaining a reaction mixture in an unsealed environment at a predetermined volume are particularly valuable for performing a PCR reaction, since PCR utilizes a number of different steps, performed at different temperatures, including temperatures as high as 95° C. Thus, the disclosed methods provide a means to monitor the reaction volume at different times during the PCR reaction and dispense liquid, generally water, to the target site in order to maintain the reaction at a predetermined volume.

The disclosed methods for synthesizing a biopolymer in a submicroliter reaction also can be used to synthesize a polypeptide. The disclosed methods also can be used to synthesize a carbohydrate, a glycoprotein, a proteoglycan or a lipid in a submicroliter reaction mixture.

Diagnostics

Genetic factors may contribute to virtually every human disease, conferring susceptibility or resistance, affecting the severity or progression of disease, and interacting with environmental influences. much of current biomedical research, in the public and private sectors, is based upon the expectation that understanding the genetic contribution to disease will revolutionize diagnosis, treatment, and prevention. Analysis of DNA sequence variation is becoming an increasingly important source of information for identifying the genes involved in disease and in normal biological processes such as development, aging and reproduction.

Genomic research has identified several types of DNA sequence variations, including insertions and deletions, differences in the copy number of repeated sequences, and single base pair differences such as single base pair deletions, termed single nucleotide polymorphisms (SNPs). SNPs occur with a frequency of about 1% (or about 1 million SNPs) in the human genome and serve as markers of regions in the human genome. While biological processes and diseases are caused or influenced by complex interactions among multiple genes and environmental factors, many alleles associated with health problems may have low penetrance, meaning that only a few of the individuals carrying them will develop disease. SNPs better identify regions important for mapping and discovering the genes associated with common diseases. In addition to their frequency, SNPs are attractive candidates as genetic markers due to their stability, generally having much lower mutation rates, and the amenability of automating the analysis of such sequences, thereby allowing large scale genetic analysis.

The screening and scoring of the million or so SNPs and the genetic loci predicted make up the human genome largely is dependent on the scientific community's ability to reduce the cost of such analysis. Over the past few years, scientists have begun to develop methods such as multiplexing, which allow the analysis of more than one genetic locus per sample. Further development of such methods has led to the use of nanotechnology, which has miniaturized sample preparation and biochemical reactions, allowing significant cost savings and movement of DNA analysis toward automation. The open systems and methods disclosed herein provide a substantial step forward in adapting nanotechnology to the analysis of biopolymers, including in situ biopolymer synthesis and sequencing, and diagnostic assays such as oligonucleotide based primer extension reactions and PCR.

Methods of Detecting the Presence of a Biopolymer

The disclosed methods of performing a reaction in a submicroliter volume in an unsealed environment are useful for detecting the presence of the biopolymer, which can be in a biological sample, because of the ability to perform such assays with only a small amount of sample. As such, the disclosed methods are particularly useful for performing clinical diagnostic assays.

The biopolymer can be, for example, a polynucleotide, which is immobilized to the solid support and detected by identifying a detector oligonucleotide that hybridizes to the biopolymer. The detector oligonucleotide can be a peptide nucleic acid. The method can be performed with a plurality of reaction mixtures, wherein one or more of the plurality of reaction mixtures contains a biopolymer, which can be immobilized to the solid support. In such a method, the solid support can be a microchip, and the plurality of reaction mixtures is present in an array on the microchip.

Any component of the reaction mixture can be detected, as desired, including, for example, the biopolymer, which detected directly or indirectly. For example, where the biopolymer is a polynucleotide, it can be detected by identifying an amplification product produced from the polynucleotide, or by identifying a reagent such as an oligonucleotide that binds specifically to the biopolymer. The oligonucleotide can include a PNA portion, and can be an oligonucleotide primer that has been extended due to the activity of a polymerase. Where the biopolymer is a polypeptide, the reagent can be a second polypeptide that binds specifically to the first polypeptide, for example, an antibody.

The disclosed methods of performing a reaction in a submicroliter volume in an unsealed environment also can be used to examine a polynucleotide using a primer extension reaction. The primer extension reaction can be competitive oligonucleotide single base extension; primer oligo base extension (PROBE); loop-PROBE; or telomeric repeat amplification protocol, and the primer can be any oligonucleotide, including, for example, an oligonucleotide containing a peptide nucleic acid portion and having a 3' terminus that is a substrate for a polymerization reaction (see, e.g., International PCT application No. WO98/2001 9).

Such methods provide diagnostic assays, including assays for detecting the presence of, or predisposition to a disease or condition. Such a disease or condition can be a genetic disease, for example, Huntington's disease, prostate cancer, Fragile X syndrome type A, myotonic dystrophy type I, Kennedy's disease, Machado-Joseph disease, dentatorubral and pallidolyusian atrophy, and spino bulbar muscular atrophy; or the condition can be aging, which can be identified by examining the number of nucleotide repeats in telomere nucleic acid from a subject. The disease or condition also can be associated with a gene such as genes encoding BRCA1, BRCA2, APC; a gene encoding dystrophin,β-globin, Factor IX, Factor VIIc, ornithine-d-aminotransferase, hypoxanthine guanine phosphoribosyl transferase, or the cystic fibrosis transmembrane receptor (CFTR); or a proto-oncogene.

The methods as disclosed herein also are useful for detecting single nucleotide polymorphisms (SNPs), which occur with a frequency of about 1% (or about 1 million SNPs) in the human genome and serve as markers of regions in the human genome. SNPs can identify regions important for mapping and discovering the genes associated with common diseases, and are attractive candidates for analysis because of their frequency in the human genome and because of their relatively low mutation rates. As such, analysis of SNPs is amenable to automation.

A method as disclosed herein can be used to genotype a subject by determining the identity of one or more allelic variants of one or more polymorphic regions in one or more genes in the subject. For example, the one or more genes can be associated with graft rejection and the process can be used to determine compatibility between a donor and a recipient of a graft. Such genes can be MHC genes, for example. Genotyping a subject using a process as provided herein can be used for forensic or identity testing purposes and the polymorphic regions can be present in mitochondrial genes or can be short tandem repeats.

A disclosed method also can be used to determine whether a subject is infected with an infectious organism such as a virus, bacterium, fungus or protist. A process for determining the isotype of an infectious organism also is provided. Thus, depending on the sequence to be detected, the methods disclosed herein are useful, for example, to diagnose a genetic disease or chromosomal abnormality; a predisposition to or an early indication of a gene influenced disease or condition, for example, obesity, atherosclerosis, diabetes or cancer; or an infection by a pathogenic organism, for example, a virus, bacterium, parasite or fungus; or to provide information relating to identity, heredity or compatibility using, for example, mini-satellite or micro-satellite sequences or HLA phenotyping.

Libraries

The disclosed methods for performing a reaction in an unsealed environment are useful for producing libraries containing diverse populations of molecules, including chemical or biological molecules such as simple or complex organic molecules, peptides, proteins, peptidomimetics, glycoproteins, lipoproteins, polynucleotides, and the like. Libraries containing such molecules and methods of making libraries, such as combinatorial libraries, are known in the art (see, for example, Huse, U.S. Pat. No. 5,264,563; Gallop et al., *J. Med. Chem.* 37:1233–1251 (1994); Gordon et al., *J. Med. Chem.* 37:1385–1401 (1994); Blondelle et al., *Trends Anal. Chem.* 14:83–92 (1995); Eichler and Houghten, *Molec. Med. Today* 1:174–180 (1995); York et al., *Science* 274:1520–1522 (1996); Gold et al., *Proc. Natl. Acad. Sci., USA* 94:59–64 (1997); Gold, U.S. Pat. No. 5,270,163, issued Dec. 14, 1993).

Libraries, such as combinatorial libraries, can contain as many as $10^{14}$ to $10^{15}$ different molecules, and typically contain on the order of $10^3$–$10^6$. The diverse molecules in a combinatorial library can be based, for example, on a known molecule, such as known pharmacophore scaffold, which is being diversified to find a new, but similar molecule having more desirable characteristics such as better solubility or the ability to be administered orally or bioactivity. Of course, the diverse molecules also can be randomly designed molecules, which can be screened for a desirable characteristics.

The methods herein allow libraries of diverse molecules to be produced in an open system and, if desired, using a single tube format. In addition, the diverse molecules produced can be screened in situ, for example, where the library is a library of diverse antibodies, they can be screened using the appropriate antigen and a suitable binding assay; or where the library is a library of diverse drugs, which are based on a drug that can inhibit a protein-protein interaction involved, for example, in a metabolic pathway associated with a disease, the diverse drugs can be screened by contacting a drug with the proteins and monitoring the association of the proteins. A screening assay provides a simple means for identifying those agents in the library that have a desirable property. Thus, a screening assay can be performed following preparation of a combinatorial library, and the entire process can be automated using an open system as disclosed, thereby allowing for high through-put screening assays.

The following examples are included for illustrative purposes only and are not intended to limit the scope of the invention.

EXAMPLE 1

Unsealed Nanoliter PCR Monitored by Fluorescence Energy Transfer Assay in a Single Well Procedure This example demonstrates that a PCR amplification performed in an open system can be detected online by increasing fluorescence using a fluorescence energy transfer assay, the TaqMan™ assay (*Nucleic Acids Res.* 25:1999–2004 (1997)).

The TaqMan™ fluorescent assay uses an oligonucleotide probe complementary to an internal segment of the target DNA to be amplified. The probe is labeled with two fluorescent moieties. As a result of the overlap between the emission and excitation spectra of the two fluorescent moieties, one moiety quenches the emission of the other moiety. The presence of this probe during PCR allows the amplification process to be monitored. The probe hybridizes to the target DNA during the PCR process and becomes susceptible to degradation by the 5' nuclease activity of Taq polymerase, which is specific for DNA hybridized to the template. As a result of the nucleolytic degradation, the two fluorescent labels are no longer in proximity, thereby reducing the quenching and increasing the intensity of the emitted light. As a result, measurement of fluorescence during amplification permits real-time monitoring of the PCR yield.

A TaqMan™ kit (Applied Biosystems, Foster City Calif.) contains the following components: human genomic DNA at a concentration of 10 ng/μl, forward and reverse primers specific for the human β-actin gene: forward primer 5'-TCACCCACACTGTGCCCATCTACGA-3' (SEQ ID No. 1); and reverse primer (5'-CAGCGGAACCGCTCATTGCCAATGG-3' (SEQ ID No. 2); a dual fluorophore-labeled probe: 5'-(6-carboxyfluorescein)-ATGCCC-(6-carboxytetramethylrhodamine)-CCCCCATGCCATCCTGCGT-3' (SEQ ID No. 3)

complementary to the β-actin specific PCR product. The reaction mixture contains 10 mM Tris-HCl (pH 8.3), 50 mM KCl, 0.01% gelatin, 1 mg/ml bovine serum albumin (BSA), 3.5 mM $MgCl_2$, 200 μM of each dNTP, 300 μM of the forward and reverse amplification primers, 200 μM of the dual fluorophore-labeled probe, 0.5 Units Taq polymerase, 0.1 Units anti-Taq antibody and 5 ng of template DNA in μl total volume. PCR is performed using the following cycling conditions: 40 cycles of 94° C. for 10 seconds, 54° C. for 5 seconds, and 72° C. for 15 seconds.

PCR was performed on a modified 2 channel NANO-PLOTTER pipetting device type NP1c (GeSim, Dresden Germany). This fluid dispenser device has an xyz table to move and dispense liquids from a piezo electric pipette. The pipettes are connected to pump system (diluters) to fill the pipettes with liquid in the nanoliter scale from a microliter plate deposited on the z-table of the pipetting device. The other end of the diluters are connected to a reservoir which contains system liquid, for example, 50 ml ultrapure water. Valve settings in the diluters allows to bypass system liquids to the piezo electric pipettes.

The NANO-PLOTTER (GeSiM, Germany), discussed above, is modified so that the target sites includes a 22W Peltier heating/cooling element, or other such element, which is controlled by a programmable thermoelectric temperature controller LFI-3526 (Wavelength Electronic, Inc., Bozeman Mont.). Modification with reference to the NANO-PLOTTER refers to coupling the device with a heating element to heat the liquid before it is dispensed onto the chip support. This can be effected by heating of the microtiter dish or heating the source of the water, such as the reservoir. Temperature is measured using a PT 500 type F3132 (Newport Electronics, Deckenpfronn Germany). System liquid is heated to target temperature directly in the pipette to keep the temperature gradient between reaction liquid on the target and subsequently added system liquid zero.

The reaction is deposited on two different positions on a microchip support (which will be sold under the trademark Spectrochip™ by Sequenom, Inc., San Diego Calif.), which has a hydrophobic surface with hydrophilic target sites for retaining aqueous reaction mixtures. The chip support contemplated in this example, includes two modified hydrophobic positions that allow the reaction liquid to grow only in the z-direction. One position on the chip is used to monitor the reaction using a fiber optic set very close to the reaction position. The fiber optic is connected to a photomultiplier to convert the fluorescence signal to an electric signal. The bandpass filter is placed between the fiber optic and the photomultiplier to cut-off the exciting wavelength. Fluorescence is excited with a 15 mW argon laser and detected through the recommended bandpass filter(Applied Biosystems).

The second position on the chip (dummy position) is used to monitor the liquid loss due to evaporation. An inter digital array is set very close to the dummy position in order to monitor drop size by capacity measurements. The reaction mix and the dummy drop are kept constant during each PCR cycle by adjusting the dispensing frequency of the system liquid. Since the capacity can be changed in both directions, when the drop volume increased or decreased, the frequency of added reservoir liquid is related to the cycle program, so that the slope of frequency is negative when the cycle temperature is decreased and is positive when the cycle temperature is increased. The whole system can be covered and darkened to reduce background effect while obtaining the fluorescence signal.

Five nl (25 drops) of reaction mix and dummy liquid are transferred from a microtiter plate onto a cooled (5° C.) 2-position silicon Spectrochip™ microchip. This cooled trap is used to determine the initial drop size, without evaporation. Once the initial drop size is determined the PCR program is started. During PCR, the pipettes replace evaporated water from the system liquid based on the measured capacity and fluorescence signal, as obtained online. Liquid loss also can be monitored by laser scan microscopy, where the whole dummy drop is irradiated by a He—Ne laser (632 nm) and monitored (Fraunhofer Inst., Erlangen Germany). Each deviation of drop size is recognized and liquid is dispensed accordingly.

For a 97 tube procedure, including 96 reactions and one dummy reaction, 97 very small laser diodes (2×2 mm) are placed under the target sites to excite fluorescence in the reaction volume from behind. An advantage of this system is that each of the 97 reactions can be monitored at the same time without scanning the argon laser over the whole chip. The reaction volume is dispensed onto a glass pad, and the laser diode is mounted under the Peltier element to provide the diode with its working temperature, because the storage temperature of a laser diode is lower than the temperature used in a reaction such as PCR and, therefore, cannot be placed between the target and the peltier element. Thus, the Peltier element is constructed with holes to allow passage of the focused laser beam. A 97 diode array also can be placed at a different location.

The same experiment, in a 97 tube or 385 tube format, can be performed using two different blocks, containing active and passive piezo electric pipettes. The active block contains 1, 4 or 8 pipettes and the includes a system to transfer samples from a microliter plate. The passive black contains 97 (385) pipettes (including the dummy tip) with the same measurements as the Spectrochip™ microchip. Each piezo electric pipette of the active/passive block is addressable with its own piezo electric dispensing parameters. With the passive block, system liquid is added simultaneously onto each of the 97 (385) positions of the chip.

EXAMPLE 2

Unsealed Nanoliter PCT Prior to MALDI-MS Analysis in a Single Tube Procedure

This example demonstrates that PCR products produced in an unsealed environment can be detected using matrix assisted laser desorption ionization (MALDI) mass spectrometry.

PCR is performed using pACT template, which is a pUC derivative harboring a 389 bp insert of human β-actin cDNA, biotinylated primer BAct2 d(bio-GAC TGA CTA CCT CAT GAA GAT CC) (SEQ ID No. 4) and non-biotinylated primer Act4 d(GAA GCT GTA GCC GCG CTC GG) (SEQ ID No. 5). The reaction mix contains 5 μl 10× PCR buffer (200 mM Tris-HCl (pH 8.75), 100 mM KCl, 100 mM $(NH_4)_2SO_4$, 20 mM $MgSO_4$, 1% Triton X-100, 1 mg BSA), a final concentration of 200 μM of each dNTP, 10 pmol biotinylated primer, 100 pmol non-biotinylated primer, 2.5 Units Pfu DNA polymerase (Stratagene; La Jolla Calif.), 0.25 ng of template, and water to a final volume of 50 μl. Amplification cycles were as follows: 30 cycles of 94° C. for 30 seconds, 65° C. for 30 seconds, and 72° C. for 30 seconds.

PCR was performed using a 1 channel NANO-PLOTTER pipetting device type NP1C (GeSim, Dresden Germany) modified with a heating element as described herein. This pipetting device has an xyz table to move and dispense liquids from a piezo electric pipette. The pipette is connected to a pump system (diluter) to fill the pipette with liquid in the nanoliter scale from a microliter plate deposited on the z-table of the pipetting device. The other end of the diluter is connected to a reservoir that contains system liquid, for example, 50 ml ultrapure water. Valve settings in the diluter allow the bypass of system liquid to the piezo electric pipette. It is modified for use herein such that the target site (site to which liquid is dispensed) of the pipetting device has a 22W peltier heating/cooling element that is controlled by a programmable thermoelectric temperature controller LFI-3526 (Wavelength Electronic, Inc., Bozeman Mont.). Temperature is measured using a PT 500 type F3132 (Newport Electronics, Inc., Deckenpfronn Germany).

System liquid is heated to target temperature direct in the pipette to keep the temperature gradient between reaction liquid on the target and subsequently added system liquid zero. The reaction mix is deposited on two different positions on a Spectrochip™ microchip, which contains two hydrophilic modified positions. These target sites are surrounded by a hollow of black silicon containing a dense "forest" of 10 μm high needles. Due to the sharp edge between the target site and the hollow, the reaction volume grows only in the z-direction to a defined volume. Under the position where PCR occurs, a small magnet is mounted to capture paramagnetic beads, for example, streptavidin coated paramagnetic beads.

The second position (dummy position) is used to monitor the liquid lost due to evaporation. An inter digital array is set very close to this position to monitor drop size based on capacity measurement. The reaction mix and the dummy drop are kept constant during each PCR cycle by adjusting the dispensing frequency of the system liquid (see Example 1).

Five nl (25 drops) reaction mix are transferred from a microtiter plate onto the cooled (5° C.) Spectrochip™ microchip. The cooled trap is used to determine the initial drop height without evaporation. Once the mixture is deposited, the initial height of the reaction liquid is measured and PCR program was started. Following PCR, the Spectrochip™ microchip is cooled to 5° C. to trap the reaction liquid. In a first step after PCR, the piezo electric pipette transfers 10 nl streptavidin dynabeads (M-280) from a microtiter plate into the reaction mixture to capture PCR product. In a second step, the piezo electric pipette is used to flood the target area with 1 μl of 0.07 M ammonium citrate solution to rinse the reaction mix into the hollow. The washing step is repeated once. In a third step, the PCR product is denatured from the beads using ammonia at room temperature (RT). Thus, the target was adjusted to RT and the piezo electric pipette picks up 10% ammonia and transferred 50 nl onto the target site. In the fourth step, the target is cooled to 5° C. and the denatured PCR product is redissolved with 3 nl ultrapure water. In the last step, 6 nl matrix is added into the liquid PCR product, while again adjusting the target temperature to RT to obtain optimal crystallization. The SpectroChip™ support then is transferred into a mass spectrometer (Bruker/Sequenom, Germany), which allows automated measurement of the nanoliter reactions.

The reaction also can be monitored using a He—Ne laser, and can be performed using active and passive piezo electric pipettes as disclosed in Example 1. Using a 4 channel NANO-PLOTTER pipetting device, the last 4 steps as described in Example 1 can be reduced to 2 steps, including a first step, wherein pipette 1 contains the beads and pipette 2 contains the rinse liquid, and a second step, wherein pipette 3 contains the ammonia and pipette 4 contains the matrix. Utilizing two steps prevents the ammonia from evaporation and the matrix from crystallization.

EXAMPLE 3

Unsealed Nanoliter Cycle Sequencing Prior to MALDI-MS Analysis in a One Well Procedure This example demonstrates that cycle sequencing can be performed in a single well and the reaction product subsequently can be analyzed by MALDI-MS. Using the open method, no cover or sealing is used to prevent evaporation during the cycling program for the DNA sequencing reaction.

Reactions were performed essentially as described previously (see van den Boom et al., *Anal. Biochem.*; van den Boom et al., *J.B.B.M.* standard cycle sequencing paper; Koster et al., *Nature Biotech.*; Little et al., *Anal. Chem.* 69:4540–4546 (1997)). DNA sequencing of PCR products are amplified off-line on a microchip without sealing. Target DNA to be sequenced was amplified from genomic DNA or cDNA using a biotinylated primer. The corresponding PCR product was stored in a microtiter plate accessible for the piezoelectric pipette. PCR product can be placed on each position of a 96 Spectrochip™ support, thus allowing a series of cycle sequencing reactions to be performed according to a primer walking strategy, which yields the full sequence of the PCR product.

Sequence analysis is performed by a thermal cycled reaction using a short oligonucleotide primer complementary to the biotinylated PCR strand, a DNA polymerase and a sequencing nucleotide mix in a buffered reaction system. After completion of the reaction, the biotinylated PCR template strand is immobilized to streptavidin coated magnetic beads. The sequencing ladder that hybridizes to this strand is co-immobilized and can be separated form reaction components. After a washing step, the sequencing ladder is recovered from the streptavidin beads by denaturation. In a subsequent step, the sequence ladder can be mass analyzed directly from the SpectroChip™ support using a Bruker/Sequenom MALDI-TOF MS.

The following reagents were used: p53 specific PCR product: amplification primers d(CTGCTTGCCACAGGTCTC) (SEQ ID No. 6) and d(biotin-CACAGCAGGCCAGTGTGC) (SEQ ID No. 7) were targeted against exon 7 of the p53 gene. PCR was performed according to standard procedures using 10 pmol of forward primer and 6 pmol of biotinylated reverse primer. Sequencing primer specific for the exon 7 PCR product was d(gaggcccatcctcacc) (SEQ ID No. 8). The cycle sequencing reaction mixture contained 10 mM Tris-HCl (pH 8.3), 0.01% gelatin, 1 mg/ml BSA, 3.5 mM $MgCl_2$, 200 μM of each dNTP, 300 μM of sequencing primer, 1 Unit ThermoSequenase™ and 5 ng of p53 PCR product in a 10 μl total volume. M-280 streptavidin coated paramagnetic beads also were used. Cycle sequencing was performed using the following cycling conditions: 30 cycles of 94° C. for 10 seconds, 54° C. for 5 seconds, and 72° C. for 15 seconds.

Liquid handling was performed using a 2 channel NANO-PLOTTER pipetting device type NP1c (GeSim) modified with heating element. As noted above, this device contains an xyz table to move and dispense liquids from a piezoelectric pipette. The pipettes are connected to pump systems (diluters) to fill the pipettes with liquid in nanoliter volumes from a microliter plate deposited on the z-table of the pipetting device. The other end of the diluters is connected to a reservoir containing the system liquid, 50 ml ultrapure water. Valve settings in the diluters allow to bypass system liquids to the piezo electric pipettes. The target site of the modified NANO-PLOTTER pipetting device has a 22W Peltier heating/cooling element controlled by a programmable thermoelectric temperature controller LFI-3526. Temperature is measured via PT 500 type F3132 (see Examples 1 and 2).

System liquid is heated to target temperature directly in the pipette to keep the temperature gradient between reaction liquid on the target and subsequently added system liquid zero. The reaction liquid is deposited on two different positions on a microchip support (e.g., a SpectroChip™ chip), which contains 2 hydrophilic modified positions (see Example 2). Under the position where the reaction takes place, a small magnet is mounted to capture paramagnetic beads. A second dummy position is included as described in Examples 1 and 2.

Five nl reaction mixtures are transferred from a microtiter plate onto a cooled (5° C.) Sequenom 97 position silicon SpectroChip™ microchip and the initial height of the reaction liquid is determined (see Examples 1 and 2). After the cycled sequencing reaction is completed, the SpectroChip™ microchip is cooled to 5° C. to trap the reaction liquid.

In a first step the piezo electric pipette transfers 10 nl streptavidin coated paramagnetic beads from the microliter plate into the reaction mix to separate the sequencing ladder from reaction components. The second step is to flood the working area via the piezo electric pipette with 1 µl of 0.07 M ammonium citrate to rinse the reaction mix into the hollow; this step is repeated once. The third step is to denature the sequencing ladder from the beads with 10% ammonium hydroxide solution at room temperature. The target temperature is adjusted to RT and the piezo electric transfers 10 nl ammonia onto the working area. The fourth step is to cool the target again to 5° C. and redissolve the denatured sequencing products with nl ultrapure water. In the last step, 6 nl matrix is added into the liquid sequencing products while driving the target temperature again to RT to obtain optimal crystallization. The entire SpectroChip™ microchip is transferred into a Bruker/Sequenom mass spectrometer, which allows automated measurement from the nanoliter spots.

EXAMPLE 4

RNAse Digest of Ribo-Modified Oligonuclotides in a Single Tube Reaction

Liquid handling is performed using a modified 2 channel pipetting device type NP1c described in Example 1. The target site of the modified pipetting device has a 22W Peltier heating/cooling element controlled by a programmable thermoelectric temperature controller LFI-3526, and temperature is measured using PT 500 type F3132 (see Example 1).

System liquid is heated to target temperature directly in the pipette. The reaction liquid is deposited on two different positions on the SpectroChip™ microchip, which contains two modified hydrophobic positions to allow the reaction liquid to grow only in z-direction. One position was used as the reaction position and the second position is a dummy position to monitor the liquid loss due to evaporation (see Example 1).

Twenty nl (50 pmol) of a ribo-modified oligonucleotide is placed on the reaction position of the 96 position SpectroChip™ microchip, while the chip temperature is maintained at 5° C. The cooled trap for the reaction liquid is used to determine the initial drop height without evaporation. From a microtiter plate, 20 nl of bovine pancreas RNase (Boehringer Mannheim) is added to the reaction position. The chip then is heated to a constant temperature of 37° C. for 15 min. Following completion of the reaction, the system is cooled to 4° C. and 25 nl of matrix is added, while driving the target temperature to RT to obtain optimal crystallization. The SpectroChip™ microchip is transferred into a Bruker/Sequenom mass spectrometer for automated analysis.

The detection of degraded fragments with a mass of 4524 Daltons (Da) indicates cleavage of the oligonucleotide at the modified site.
Sequence: CGAAXTCGAGCTCGGTACCC
Ribo-modification: X is rU.

EXAMPLE 5

Exonucleolytic Degradation of Oligonucleotides in a 12 Well Procedure

Liquid handling is performed on a modified 1 channel pipetting device type NP1c (GeSim, Dresden Germany). As noted, this pipetting device has a xyz table to move and dispense liquids from a piezoelectric pipette. The active piezoelectric pipette is mounted on the active block, i.e. the pipette is able to pick up samples from a microtiter plate prior to dispensing reagent onto a silicon chip support (a SpectroChip™ support). 97 pipettes with the same measurements as the SpectroChip™ support are connected to the passive block. With the passive block, system liquid can be added simultaneously to each of the 97 positions of the chip. The active and the passive pipettes are connected to their own pump system (diluter). Each piezo electric pipette of the active/passive block is addressable with its own piezo electric dispensing parameters in order to do pipette selection. The other ends of the diluters are connected to a reservoir which contains system liquid (50 mL ultrapure water). Valve settings in the diluters allow to bypass system liquid to the piezo electric pipette(s). The target site of the modified pipetting device has a 22W Peltier heating/cooling element which is controlled by a programmable thermoelectric temperature controller LFI-3526, and temperature is measured via PT 500 type F3132.

System liquid is heated to target temperature directly in the pipettes of the passive block to keep the temperature gradient between reaction liquid on the target and subsequently added system liquid zero. The SpectroChip™ microchip includes 97 modified hydrophobic positions, which allow the reaction liquid to grow only in z-direction; 96 positions can be used as reaction positions and the 97th position is a dummy position to monitor the liquid loss due to evaporation (see Example 1).

Using the active piezo electric pipette, 20 nl (50 pmol) of an oligonucleotide is placed on 12 positions of the 97 SpectroChip™ microchip, while the chip temperature is kept at 5° C., then 20 nl of snake venom phosphodiesterase (Boehringer Mannheim) is added to the 12 positions. The cooled trap for the reaction liquid is used to determine the initial drop high without evaporation. The SpectroChip™ microchip then is heated to a constant temperature of 37° C. In order to obtain a kinetic picture of the degradation reaction, the patches are allowed to dry sequentially two minutes after another. The drying process is monitored and controlled using a capacitor measurement system; system liquid replacement utilizes the passive piezo electric pipettes.

After all reactions are completed, the chip is cooled to 5° C. and the analyte is redissolved using the passive piezo electric pipette block. Matrix is added to the 12 positions, while driving the target temperature to RT to obtain the best crystallization results. The SpectroChip™ microchip then is transferred into a Bruker/Sequenom mass spectrometer which allows automated measurement from nanoliter spots, resulting in twelve spectra representing the whole oligonucleotide sequence.

EXAMPLE 6

Restriction Digest of PCT Products

Liquid handling is performed on the modified 1 channel NP1c dispensing device described in Example 5. The target site of the modified NANO-PLOTTER pipetting device has a 22W peltier heating/cooling element controlled by a programmable thermoelectric temperature controller LFI3526. Temperature is measured via PT 500 type F3132 (see Example 5).

System liquid was also heated to target temperature directly in the pipettes of the passive block to keep the temperature gradient between reaction liquid on the target and subsequently added system liquid zero. The SpectroChip™ microchip is as described in Example 5.

A portion of exon 4 of the human apolipoprotein-E gene is amplified by PCR in a conventional 96 well microtiter plate (see Little et al., *Int. J. Mass Spectrom. Ion Processes* 169/170:323–330 (1997)). Aliquots of each well (30 nl) are transferred to a 97 SpectroChip™ microchip with the active piezo electric pipette block while the chip temperature is maintained at 5° C., then 20 nl of Cfol and Rsal (Boehringer Mannheim) are added to each position. The cooled trap for the reaction liquid is used to determine the initial drop high without evaporation. The chip is heated to a constant temperature of 37° C. for 15 min, during which time the reaction volume is kept constant. After the reaction, the system is cooled to 4° C. and 25 nl of matrix is added to each position, while driving the target temperature to RT for optimal crystallization. The entire SpectroChip™ microchip is transferred into a Bruker/Sequenom mass spectrometer for automated analysis of the nanoliter spots.

With respect to the genotype of the genomic DNA used as template in the PCR reactions, different fragment pattern are observed. The genotype epsilon 3 results, for example, in fragments having molecular masses of 6749 Da, 7521 Da, 14858 Da, 18839 Da, 29708 Da and 33331 Da.

EXAMPLE 7

Nanoliter Liquid Handling System For Real Time DNA Sequencing By Detection of Pyrophosphate Release Sequencing by synthesis (pyrophosphate sequencing) is performed by detecting DNA polymerase activity by an enzymatic luminometric assay, which determines the amount of inorganic pyrophosphate ("ELIDA assay"; see Ronaghi et al., *Anal. Biochem.* 267:65–71 (1999); Ronaghi et al., *Biotechniques* 25:876–878, 880–882, and 884 (1998); Ronaghi et al., *Science* 281:363–365 (1998); Ronaghi et al., *Anal.Biochem.* 242:84–89 (1996); Nyren, Anal. Biochem. 167:235–238 (1987)).

Pyrophosphate sequencing is performed as follows. Either a synthetic template or a PCR product is immobilized onto a solid support. Immobilization can be performed employing standard procedures such as the streptavidin biotin system or SIAB chemistry, as disclosed herein. In case of PCR product sequencing, the double stranded PCR product is denatured, for example, by alkaline treatment, prior to the sequencing reaction.

An oligonucleotide primer is annealed to the immobilized template strand. A DNA polymerase and one deoxynucleotide triphosphate in a buffered system are added and incorporation of the nucleotide is monitored by the release of inorganic pyrophosphate. The added nucleotide is incorporated by the polymerase only if it is complementary to the corresponding position in the template sequence. The release of pyrophosphate, a result of the incorporation of the nucleotide triphosphate, is monitored as follows: inorganic pyrophosphate is converted to ATP via the ATP sulfurylase, and the level of present ATP is monitored by the firefly luciferase system.

In the sequencing process, the addition of nucleotide triphosphates is performed in a stepwise manner. The reaction is allowed to proceed for a certain time, then the reaction mix is separated from the solid support and, therefore, from the immobilized template primer system, and further washing is performed. Following washing, the next nucleotide triphosphate is added as part of a reaction mix, containing all necessary enzymes and buffers and monitoring is performed as above. Repeating the additions with all four possible nucleotide triphosphates in a cycled manner allows stepwise (base for base) sequencing of the template strand.

Liquid handling is performed on a modified 8 channel pipetting device type NP1c from (GeSim, Dresden Germany). As noted above, this pipetting device includes an xyz table to move and dispense liquids from a piezo electric pipette. The active piezo electric pipettes are mounted on the active block, i.e. the pipettes are able to pick up samples from a microtiter plate prior to dispensing reagent onto a support, such as a microchip type support SpectroChip™ microchip. 97 pipettes with the ame measurements as the SpectroChip™ microchip are connected to the massive block. With the passive block system liquid can be added simultaneous onto each of the 97 positions of the chip.

The active and the passive pipettes are connected to their own pump system (diluter). Each piezo electric pipette of the active/passive block is addressable with its own piezo electric dispensing parameters in order to do pipette selection. The other ends of the diluters are connected to a reservoir which contains system liquid (50 ml ultrapure water). Valve settings in the diluters allow to bypass system liquid to the piezo electric pipette(s).

The target site of the modified pipetting device has a 22W Peltier heating/cooling element which is controlled by a programmable thermoelectric temperature controller LFI-3526. Temperature is measured via PT 500 type F3132. System liquid is heated to target temperature directly in the pipettes of the passive block to keep the temperature gradient between reaction liquid on the target and subsequently added system liquid zero. The SpectroChip™ microchip has 97 modified hydrophobic positions, which allow the reaction liquid to grow only in the z-direction; 96 positions can be used as reaction positions, one of which is used to monitor the reaction using, for example, a fiber optic set very close to the reaction position. The fiber optic is connected to a photomultiplier to convert the luminescence signal to an electric signal. A bandpass filter is placed between fiber optic and photomultiplier. The 97th position (dummy position) is used to monitor the liquid loss due to evaporation as described in Example 1. The whole system is covered and darkened to reduce background effect while obtaining the fluorescence signal.

The universal reaction mix contains 0.1 M Tris-acetate (pH 7.75), 2 mM EDTA, 10 mM magnesium acetate, 0.1% BSA, 1 mM dithiothreitol, 5 $\mu$M adenosine 5'-phosphosulfate (APS), 0.4 mg/ml polyvinylpyrrolidone, 100 $\mu$g/ml D-luciferin (bioOrbit, Finland), 4 $\mu$ug/ml L-Luciferin (BioOrbit, Finland), 0.3 U/ml ATP sulfurylase (ATP:sulfate adenylyltransferase; EC 2.7.7.4; Sigma Chemical Co., St. Louis, Mo.), purified luciferase (Sigma) to yield a useable luminometric response, and 2.5 U DNA polymerase (Sequenase 2.0, Amersham). Nucleotide triphosphate mixes include 4 separate mixes containing an aqueous solution of either 50 $\mu$M S-dATP, dCTP, dGTP and dTTP. Washing solution I is 10 mM Tris-HCl (pH 7.5), 0.25 M NaCl, 0.1% Tween 20. Washing solution II is 10 mM Tris-acetate (pH 7.5). Primer solution is an aqueous solution of 200 $\mu$M of sequencing primer PCR product is amplified from target DNA using a 5'-thiolated primer, amplification products are stored in a MTP and supplied to the nanoliquid handling device. PCR product is pipetted from the MTP on the chip using the piezoelectric pipette of the nanoliquid handling system. PCR product is immobilized on the chip surface via SIAB chemistry, and is denatured upon addition of 5 nl of 100 mM NaOH using the piezoelectric pipette of the nanoliquid handling system. Remaining immobilized single stranded PCR product is washed with 10 mM Tris-HCl (pH 8.0) twice.

Sequencing reactions are performed using an 8-channel piezoelectric pipette for automated performance of the cycled stepwise nucleotide addition. One pipette is filed with water, one with the reaction mix, four pipettes are necessary to contain the separate nucleotides and two pipettes contain the washing solutions. Sequencing is performed as follows:

1. The piezoelectric pipette of the nanoliquid handling system fills with the sequencing primer solution of the MTP and adds it to the immobilized template strand on the chip.
2. All 8 pipettes of the head then are filled with the respective solutions from the supply MTP.
3. The chip well is heated to 95° C. to denature secondary structure of the PCR product and is slowly cooled to RT to allow annealing of the sequencing primer. During this thermal step, evaporation is prevented by sequential addition of water droplets from a piezoelectric pipette Nr. 1.
4. The primer template hybrid is washed by addition of the washing solution I from a piezoelectric pipette Nr.2.
5. The reaction mix is added to the primer template system using the corresponding piezoelectric pipette Nr.3.
6. Upon addition of the first nucleotide (SdATP) using piezoelectric pipette Nr. 4, the incorporation reaction is initiated and luminescence is monitored; the reaction is allowed to proceed for 10 seconds, during which time the reaction volume is maintained by sequential addition of water through pipette 1. Incorporation is identified by increased luminescence. Intensities are analyzed to determine the number of sequential incorporation of the respective nucleotide.
7. The reaction is stopped by rinsing the immobilized DNA with washing solution I from pipette 2.
8. The immobilized DNA is washed by addition of washing solution II from pipette 8.
9. Reaction mix is again deposited onto the chip by pipette 3.
10. Upon addition of the second nucleotide (dCTP) using piezoelectric pipette Nr. 5, the incorporation reaction is started and the luminescence is monitored; the reaction is allowed to proceed for 10 seconds, during which time the reaction volume is kept constant by sequential addition of water through pipette 1. The incorporation is identified by increased luminescence. intensities are analyzed to determine the number of sequential incorporation of the respective nucleotide.
11. The reaction is stopped by rinsing the immobilized DNA with ashing solution I from pipette 2.
12. The immobilized DNA is washed by addition of washing solution II from pipette 8.
13. Reaction mix is again deposited onto the chip by pipette 3.
14. Upon addition of the third nucleotide (dGTP) using piezoelectric pipette Nr. 6, the incorporation reaction is started and the luminescence is monitored; the reaction is allowed to proceed for 10 seconds, during which time the reaction volume is kept constant by sequential addition of water through pipette 1. The incorporation is identified by increased luminescence. Intensities are analyzed to determine the number of sequential incorporation of the respective nucleotide.
15. The reaction is stopped by rinsing the immobilized DNA with washing solution I from pipette 2.
16. The immobilized DNA is washed by addition of washing solution II from pipette 8.
17. Reaction mix is again deposited onto the chip by pipette 3.
18. Upon addition of the fourth nucleotide (dTTP) using piezoelectric pipette Nr. 7, the incorporation reaction is started and the luminescence is monitored; the reaction is allowed to proceed for 10 seconds, during which time reaction volume is kept constant by sequential addition of water through pipette 1. The incorporation is identified by increased luminescence. Intensities are analyzed to determine the number of sequential incorporation of the respective nucleotide.
19. The reaction is stopped by rinsing the immobilized DNA with washing solution I from pipette 2.
20. The immobilized DNA is washed by addition of washing solution II from pipette 8.
21. Reaction mix is again deposited onto the chip by pipette 3.
22. The reaction scheme proceeds in a cycled manner by looping back to step 6.

While the invention has been described with some specificity, modifications apparent to those with ordinary skill in the art may be made without departing from the scope of the invention. Since such modifications will be apparent to those of skill in the art, it is intended that this invention be limited only by the scope of the appended claims.

What is claimed is:

1. An open system for performing a reaction while maintaining constant concentrations of reactants, comprising:
   a support for performing the reaction in an open environment, wherein:
   the support is for containing or retaining biopolymers or biological particles; and
   the reaction is a submicroliter volume reaction;
   a nanoliter dispensing pipette for dispensing an amount of a liquid onto the surface of the support;
   a temperature controlling device for regulating the temperature of the support; and
   means for controlling the amount of liquid dispensed, wherein:
      the amount of liquid dispensed corresponds to the amount of liquid that evaporates from the support to thereby maintain the concentration of reactants in the reaction; and
      the system is not sealed.

2. The open system of claim 1, wherein the controlling means comprises software that calculates the amount of liquid that evaporates and signals the dispensing pipette to deliver an amount of liquid that corresponds to the amount that evaporates.

3. The open system of claim 1, wherein the controlling means comprises manual input.

4. The open system of claim 1, further comprising a means for determining the temperature of a liquid on the support.

5. The open system of claim 1, wherein the support comprises a bead, pin, comb, wafer, well or microchip.

6. An open system for performing a reaction, comprising:
   a support functionalized for linking a biopolymer or biological particle and for performing the reaction, wherein the support comprises a bead, pin, comb, wafer, well or microchip;
   a nanoliter dispensing pipette for dispensing an amount of a liquid onto the surface of the support;
   a temperature controlling device for regulating the temperature of the support; and
   means for controlling the amount of liquid dispensed, wherein the amount of liquid dispensed corresponds to the amount of liquid that evaporates from the support, wherein the system is not sealed.

7. The open system of claim 1, wherein the reaction is a submicroliter reaction.

8. A system, comprising:
   a solid support having a target site for retaining or containing a liquid;
   a liquid dispensing system for dispensing a liquid to the target site;
   a temperature controlling system, which regulates the temperature of the solid support; and
   an interface for indicating an amount of liquid to be dispensed to the target site, wherein the amount of liquid to be dispensed corresponds to an amount of liquid that evaporates from the target site, wherein: the interface monitors the level of a liquid on the target site; and
   the interface comprises a light source and a photometer.

9. A system, comprising:
   a solid support having a target site for retaining or containing a liquid;
   a liquid dispensing system for dispensing a liquid to the target site;
   a temperature controlling system, which regulates the temperature of the solid support; and
   an interface for indicating an amount of liquid to be dispensed to the target site, wherein the amount of liquid to be dispensed corresponds to an amount of liquid that evaporates from the target site, wherein the interface monitors the concentration of a component in the liquid.

10. The system of claim 8, wherein the temperature controlling system comprises a Peltier element.

11. The system of claim 8, further comprising a detection system.

12. A system comprising:
    means for dispensing a liquid;
    means for containing a reaction volume comprising a microchip or glass slide, wherein the microchip or glass slide comprises on a surface, an array of hydrophilic regions and adjacent hydrophobic regions;
    means for controlling the temperature of the reaction volume containing means; and
    means for regulating an amount of liquid dispensed from the liquid dispensing means based on the temperature of the reaction volume containing means.

13. A method for performing a reaction in an unsealed environment, comprising the steps of:
    a) dispensing a predetermined submicroliter volume of liquid onto a target site on a surface of a support;
    b) determining an amount or rate of evaporation of the liquid from the target site; and
    c) dispensing a further amount of liquid to the target site, wherein the further amount dispensed corresponds to the amount of liquid that evaporates from the target site, thereby maintaining the reaction volumes and concentration of reactant at a predetermined volume throughout the course of the reaction.

14. The method of claim 13, wherein the reaction is performed in a submicroliter volume.

15. The method of claim 13, wherein the amount or rate of evaporation is determined by monitoring the temperature of the target site and calculating the amount or rate of evaporation.

16. A method for performing a reaction in an unsealed environment, comprising the steps of:
    a) dispensing a predetermined submicroliter volume of liquid onto a target site on a surface of a support;
    b) determining an amount or rate of evaporation of the liquid from the target site, wherein the amount or rate of evaporation is determined by monitoring the conductance of the liquid at the target site; and c) dispensing a further amount of liquid to the target site, wherein the further amount dispensed corresponds to the amount of liquid that evaporates from the target site, thereby maintaining the reaction volume at a predetermined volume throughout the course of the reaction.

17. A method for performing a reaction in an unsealed environment, comprising the steps of:
   a) dispensing a predetermined submicroliter volume of liquid onto a target site on a surface of a support;
   b) determining an amount or rate of evaporation of the liquid from the target site; and
   c) dispensing a further amount of liquid to the target site, wherein the further amount dispensed corresponds to the amount of liquid that evaporates from the target site, thereby maintaining the reaction volume at a predetermined volume throughout the course of the reaction, wherein the reaction is a nucleic acid amplification reaction.

18. The method of claim 13, wherein the reaction is one of a plurality of reactions.

19. A method for performing a reaction in an unsealed environment, comprising the steps of:
   a) dispensing a predetermined submicroliter volume of liquid onto a target site on a surface of a support;
   b) determining an amount or rate of evaporation of the liquid from the target site; and
   c) dispensing a further amount of liquid to the target site, wherein the further amount dispensed corresponds to the amount of liquid that evaporates from the target site, thereby maintaining the reaction volume at a predetermined volume throughout the course of the reaction, wherein:
      the reaction is one of a plurality of reactions, and
      the plurality of reactions are performed at a single target site.

20. The method of claim 19, wherein the reactions are performed simultaneously.

21. The method of claim 20, which is a multiplex reaction.

22. The method of claim 18, wherein each reaction in the plurality is performed at a single target site.

23. A method for performing a reaction in an unsealed environment, comprising the steps of:
   a) dispensing a predetermined submicroliter volume of liquid onto a target site on a surface of a support;
   b) determining an amount or rate of evaporation of the liquid from the target site; and
   c) dispensing a further amount of liquid to the target site, wherein the further amount dispensed corresponds to the amount of liquid that evaporates from the target site, thereby maintaining the reaction volume at a predetermined volume throughout the course of the reaction, wherein:
      the reaction is one of a plurality of reactions;
      each reaction in the plurality is performed at a single target site; and
      the method comprises synthesis of a combinatorial library.

24. A method for performing a reaction in an unsealed environment, comprising the steps of:
   a) dispensing a predetermined submicroliter volume of liquid onto a target site on a surface of a support;
   b) determining an amount or rate of evaporation of the liquid from the target site; and
   c) dispensing a further amount of liquid to the target site, wherein the further amount dispensed corresponds to the amount of liquid that evaporates from the target site, thereby maintaining the reaction volume at a predetermined volume throughout the course of the reaction; and
   d) detecting a component of the reaction, detecting a component of the reaction.

25. A method for maintaining a volume of a reaction mixture on a solid support in an unsealed environment, comprising the steps of:
   a) determining the amount of liquid that evaporates from the reaction mixture; and
   b) dispensing into the reaction mixture an amount of liquid that corresponds to the amount of liquid that evaporates, thereby maintaining the volume of the reaction mixture, wherein the reaction mixture comprises a biopolymer.

26. The method of claim 25, wherein the reaction mixture comprises a biopolymer sequencing reaction.

27. The method of claim 25, wherein the biopolymer is a polynucleotide.

28. The method of claim 26, wherein the sequencing reaction comprises a chemical cleavage reaction.

29. The method of claim 26, wherein the sequencing reaction comprises an enzymatic reaction.

30. The method of claim 29, wherein the enzymatic reaction is a chain termination reaction comprising a polymerase and a chain terminating nucleoside triphosphate.

31. The method of claim 29, wherein the enzymatic reaction is an exonuclease reaction.

32. The method of claim 26, wherein the biopolymer is a polypeptide.

33. The method of claim 32, wherein the sequencing reaction is selected from the group consisting of a chemical sequencing reaction and an enzymatic sequencing reaction.

34. The method of claim 26, wherein the biopolymer is selected from the group consisting of a carbohydrate, a glycoprotein, a proteoglycan and a lipid.

35. The method of claim 25, wherein the reaction mixture comprises a biopolymer synthesis reaction.

36. The method of claim 35, wherein the biopolymer is a polynucleotide.

37. The method of claim 36, wherein the synthesis reaction is a chemical synthesis reaction.

38. The method of claim 36, wherein the synthesis reaction is an enzymatic synthesis reaction, comprising a polymerase.

39. The method of claim 38, wherein the biopolymer and the polymerase are selected from the group consisting of:
   a ribonucleic acid and an RNA dependent RNA polymerase;
   a ribonucleic acid and an RNA dependent DNA polymerase; and
   a deoxyribonucleic acid and a DNA dependent DNA polymerase.

40. The method of claim 38, comprising a ribonucleic acid, an RNA dependent DNA polymerase, and a DNA dependent DNA polymerase.

41. The method of claim 38, wherein the enzymatic synthesis reaction is a polymerase chain reaction, further comprising a set of primers.

42. The method of claim 41, wherein a primer of the set of primers comprises a peptide nucleic acid sequence.

43. The method of claim 35, wherein the biopolymer is a polypeptide.

44. The method of claim 35, wherein the biopolymer is selected from the group consisting of a carbohydrate, a glycoprotein, a proteoglycan and a lipid.

45. The method of claim 35, wherein the biopolymer is a polynucleotide and the reaction mixture comprises a primer extension reaction.

46. The method of claim 45, wherein the primer extension reaction is selected from the group consisting of:

competitive oligonucleotide single base extension;

primer oligo base extension (PROBE);

loop-PROBE; and telomeric repeat amplification.

47. The method of claim 25, wherein the reaction mixture comprises an assay for detecting the presence of the biopolymer.

48. The method of claim 47, wherein the biopolymer is obtained from a biological sample.

49. The method of claim 48, wherein the method comprises a diagnostic method for detecting the presence of or predisposition to a genetic disease or condition.

50. The method of claim 48, wherein the method comprises determining a genotype.

51. The method of claim 25, wherein the biopolymer is immobilized to the solid support.

52. The method of claim 47, comprising detecting the biopolymer by identifying a detector oligonucleotide that has hybridized to the biopolymer.

53. The method of claim 52, wherein the detector oligonucleotide comprises a peptide nucleic acid sequence.

54. A method for performing a plurality of reactions in an unsealed environments, comprising the steps of:

a) providing a plurality of reaction mixtures, wherein each reaction in the plurality is at a target site on a surface of a solid support;

b) monitoring the amount of liquid that evaporates from reaction mixtures in the plurality; and c) dispensing into the reaction mixtures an amount of liquid that corresponds to the amount of liquid that evaporates from the reaction mixtures, thereby maintaining the volume of the reaction mixtures in the plurality at a predetermined volume, wherein one or more of the reaction mixtures in the plurality comprises one or more biopolymers.

55. The method of claim 54, wherein a biopolymer present in a reaction mixture is immobilized to the solid support.

56. The method of claim 54, wherein the solid support comprises a microchip.

57. The method of claim 56, wherein the plurality of reaction mixtures is present in an array on the microchip.

58. A method for performing a plurality of reactions in an unsealed environments, comprising the steps of:

a) providing a plurality of reaction mixtures, wherein each reaction in the plurality is at a target site on a surface of a solid support;

b) monitoring the amount of liquid that evaporates from reaction mixtures in the plurality;

c) dispensing into the reaction mixtures an amount of liquid that corresponds to the amount of liquid that evaporates from the reaction mixtures, thereby maintaining the volume of the reaction mixtures in the plurality at a predetermined volume; and d) detecting a component of a reaction mixture in the plurality.

59. The method of claim 58, wherein the component is a biopolymer.

60. The method of claim 59, wherein the biopolymer is detected directly.

61. The method of claim 59, wherein the biopolymer is detected indirectly.

62. The method of claim 61, wherein the biopolymer is a polynucleotide, which is detected by detecting an amplification product produced from the polynucleotide.

63. The method of claim 61, wherein the biopolymer is detected by identifying a reagent that binds specifically to the biopolymer.

64. The method of claim 63, wherein the biopolymer is a polynucleotide and the reagent is an oligonucleotide that hybridizes specifically to the polynucleotide.

65. The method of claim 64, wherein the oligonucleotide is a primer, which has been extended due to the activity of a polymerase.

66. The method of claim 63, wherein the biopolymer is a first polypeptide and the reagent is a second polypeptide that binds specifically to the first polypeptide.

67. The method of claim 63, wherein the second polypeptide is an antibody.

68. The method of claim 58, wherein the component is detected by a method selected from mass spectrometry, spectrophotometry, and capillary electrophoresis.

69. A method for performing a plurality of reactions in an unsealed environment, comprising:

a) providing a plurality of reaction mixtures, wherein each reaction in the plurality is performed at a target site on a surface of a solid support that contains or retains the reaction mixtures;

b) monitoring the amount of liquid that evaporates from reaction mixtures in the plurality; and c) dispensing into the reaction mixtures an amount of liquid that corresponds to the amount of liquid that evaporates from the reaction mixtures, thereby maintaining the volume of the reaction mixtures in the plurality at a predetermined volume, whereby the concentrations of reactants in the reaction mixtures remain constant.

70. The system of claim 14, wherein the temperature controlling system comprises a Peltier element.

71. The system of claim 14, further comprising a detection system.

* * * * *

UNITED STATES PATENT AND TRADEMARK OFFICE
CERTIFICATE OF CORRECTION

PATENT NO. : 6,225,061 B1
DATED : May 1, 2001
INVENTOR(S) : Becker et al.

It is certified that error appears in the above-identified patent and that said Letters Patent is hereby corrected as shown below:

Column 6,
Line 28, please replace "This" with -- This is --.

Column 7,
Line 40, please replace "solids" with -- solids in --.

Column 9,
Line 2, please replace "phophorothioate" with -- phosphorothiolate --.

Please replace claims 7, 24, 70, and 71 with the following claims:

7. The open system of claim 1, further comprising a detection system for monitoring the reaction.
24. A method for performing a reaction in an unsealed environment, comprising the steps of:
   a) dispensing a predetermined submicroliter volume of liquid onto a target site on a surface of a support;
   b) determining an amount or rate of evaporation of the liquid from the target site; and
   c) dispensing a further amount of liquid to the target site, wherein the further amount dispensed corresponds to the amount of liquid that evaporates from the target site, thereby maintaining the reaction volume at a predetermined volume throughout the course of the reaction; and
   d) detecting a component of the reaction.
70. The system of claim 9, wherein the temperature controlling system comprises a Peltier element.
71. The system of claim 9, further comprising a detection system.

Signed and Sealed this

Twelfth Day of February, 2002

Attest:

Attesting Officer

JAMES E. ROGAN
*Director of the United States Patent and Trademark Office*